(12) United States Patent
Tuval et al.

(10) Patent No.: US 12,090,314 B2
(45) Date of Patent: *Sep. 17, 2024

(54) VENTRICULAR ASSIST DEVICE

(71) Applicant: Magenta Medical Ltd., Kadima (IL)

(72) Inventors: Yosi Tuval, Even Yehuda (IL); Daniel Glozman, Kfar Yona (IL); Gad Lubinsky, Ein Vered (IL)

(73) Assignee: Magenta Medical Ltd., Kadima (IL)

( * ) Notice: Subject to any disclaimer, the term of this patent is extended or adjusted under 35 U.S.C. 154(b) by 127 days.

This patent is subject to a terminal disclaimer.

(21) Appl. No.: 17/574,701

(22) Filed: Jan. 13, 2022

(65) Prior Publication Data

US 2022/0134083 A1    May 5, 2022

Related U.S. Application Data

(63) Continuation of application No. 16/277,411, filed on Feb. 15, 2019, now Pat. No. 11,260,212, which is a
(Continued)

(51) Int. Cl.
*A61M 1/00* (2006.01)
*A61M 60/139* (2021.01)
(Continued)

(52) U.S. Cl.
CPC ........ *A61M 60/414* (2021.01); *A61M 60/139* (2021.01); *A61M 60/148* (2021.01);
(Continued)

(58) Field of Classification Search
CPC .... A61M 1/122; A61M 1/1086; A61M 1/125; A61M 2205/3334; A61M 1/1031;
(Continued)

(56) References Cited

U.S. PATENT DOCUMENTS 3,592,183 A    7/1971    Watkins et al.
4,625,712 A    12/1986   Wampler
(Continued)

FOREIGN PATENT DOCUMENTS

AU    2013205145 A1    5/2013
CA    2701809 A1    4/2009
(Continued)

OTHER PUBLICATIONS

Corrected Notice of Allowability for U.S. Appl. No. 16/810,121 mailed Jun. 28, 2022.
(Continued)

*Primary Examiner* — Deborah L Malamud
(74) *Attorney, Agent, or Firm* — Dorsey & Whitney LLP

(57) ABSTRACT

Apparatus and methods are described including a tube configured to traverse an aortic valve of a subject. A frame is disposed within at least a portion of the tube. An impeller rotates such as to pump blood from the subject's left ventricle to the subject's aorta. The impeller is disposed inside the tube such that, when the impeller and the tube are deployed inside the subject, and prior to rotation of the impeller, a gap between an outer edge of the impeller and an inner surface of the tube is less than 1 mm. A rigid stabilizing element stabilizes the impeller with respect to the tube, such that during rotation of the impeller, a gap between the outer edge of the impeller and the inner surface of the tube is maintained. Other applications are also described.

21 Claims, 10 Drawing Sheets

Related U.S. Application Data continuation of application No. PCT/IL2017/051158, filed on Oct. 23, 2017.

(60) Provisional application No. 62/412,631, filed on Oct. 25, 2016, provisional application No. 62/543,540, filed on Aug. 10, 2017.

(51) Int. Cl.
*A61M 60/148* (2021.01)
*A61M 60/17* (2021.01)
*A61M 60/237* (2021.01)
*A61M 60/414* (2021.01)
*A61M 60/806* (2021.01)
*A61M 60/825* (2021.01)

(52) U.S. Cl.
CPC .......... *A61M 60/17* (2021.01); *A61M 60/237* (2021.01); *A61M 60/806* (2021.01); *A61M 60/825* (2021.01); A61M 2205/3334 (2013.01); A61M 2230/30 (2013.01)

(58) Field of Classification Search
CPC .. A61M 2205/3327; A61M 2205/3365; A61M 25/00; A61M 2205/04; A61M 5/14276; A61N 1/05

See application file for complete search history.

(56) References Cited

U.S. PATENT DOCUMENTS

| | | |
|---|---|---|
| 4,753,221 A | 6/1988 | Kensey et al. |
| 4,919,647 A | 4/1990 | Nash |
| 4,944,722 A | 7/1990 | Carriker et al. |
| 4,954,055 A | 9/1990 | Raible et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 5,011,469 A | 4/1991 | Buckberg et al. |
| 5,061,256 A | 10/1991 | Wampler |
| 5,169,378 A | 12/1992 | Figuera |
| 5,275,580 A | 1/1994 | Yamazaki |
| 5,348,545 A | 9/1994 | Shani et al. |
| 5,507,629 A | 4/1996 | Jarvik |
| 5,531,789 A | 7/1996 | Yamazaki et al. |
| 5,569,275 A | 10/1996 | Kotula et al. |
| 5,613,935 A | 3/1997 | Jarvik |
| 5,692,882 A | 12/1997 | Bozeman et al. |
| 5,713,730 A | 2/1998 | Nose et al. |
| 5,749,855 A | 5/1998 | Reitan |
| 5,772,693 A | 6/1998 | Brownlee |
| 5,843,158 A | 12/1998 | Lenker et al. |
| 5,863,179 A | 1/1999 | Westphal et al. |
| 5,876,385 A | 3/1999 | Ikari et al. |
| 5,879,499 A | 3/1999 | Corvi |
| 5,911,685 A | 6/1999 | Siess et al. |
| 5,928,132 A | 7/1999 | Leschinsky |
| 5,947,892 A | 9/1999 | Benkowski et al. |
| 5,964,694 A | 10/1999 | Siess et al. |
| 6,007,478 A | 12/1999 | Siess et al. |
| 6,086,527 A | 7/2000 | Talpade |
| 6,116,862 A | 9/2000 | Rau et al. |
| 6,135,729 A | 10/2000 | Aber |
| 6,136,025 A | 10/2000 | Barbut et al. |
| 6,162,017 A | 12/2000 | Raible |
| 6,176,848 B1 | 1/2001 | Rau et al. |
| 6,183,220 B1 | 2/2001 | Ohara et al. |
| 6,217,541 B1 | 4/2001 | Yu |
| 6,247,892 B1 | 6/2001 | Kazatchkov et al. |
| 6,355,001 B1 | 3/2002 | Quinn et al. |
| 6,413,222 B1 | 7/2002 | Pantages et al. |
| 6,482,228 B1 | 11/2002 | Norred |
| 6,506,146 B1 | 1/2003 | Mohl |
| 6,533,716 B1 | 3/2003 | Schmutz-Rode et al. |
| 6,537,315 B2 | 3/2003 | Yamazaki et al. |
| 6,544,216 B1 | 4/2003 | Sammler et al. |
| 6,592,567 B1 | 7/2003 | Levin et al. |
| 6,616,624 B1 | 9/2003 | Kieval |
| 6,884,210 B2 | 4/2005 | Nose et al. |
| 6,949,066 B2 | 9/2005 | Bearnson et al. |
| 7,004,925 B2 | 2/2006 | Navia et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,070,555 B2 | 7/2006 | Siess |
| 7,144,364 B2 | 12/2006 | Barbut et al. |
| 7,159,593 B2 | 1/2007 | McCarthy et al. |
| 7,201,772 B2 | 4/2007 | Schwammenthal et al. |
| 7,258,679 B2 | 8/2007 | Moore et al. |
| 7,335,192 B2 | 2/2008 | Keren et al. |
| 7,338,521 B2 | 3/2008 | Antaki et al. |
| 7,341,570 B2 | 3/2008 | Keren et al. |
| 7,393,181 B2 | 7/2008 | McBride et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,878,967 B1 | 2/2011 | Khanal |
| 7,914,436 B1 | 3/2011 | Kung |
| 7,914,503 B2 | 3/2011 | Goodson et al. |
| 7,927,068 B2 | 4/2011 | McBride et al. |
| 8,012,121 B2 | 9/2011 | Goodson et al. |
| 8,079,948 B2 | 12/2011 | Shifflette |
| 8,118,723 B2 | 2/2012 | Richardson et al. |
| 8,123,669 B2 | 2/2012 | Siess et al. |
| 8,157,758 B2 | 4/2012 | Pecor et al. |
| 8,192,451 B2 | 6/2012 | Cambronne et al. |
| 8,216,122 B2 | 7/2012 | Kung |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | McBride et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,512,262 B2 | 8/2013 | Gertner |
| 8,535,211 B2 | 9/2013 | Walters et al. |
| 8,538,535 B2 | 9/2013 | Ariav et al. |
| 8,579,858 B2 | 11/2013 | Reitan et al. |
| 8,591,393 B2 | 11/2013 | Walters et al. |
| 8,591,539 B2 | 11/2013 | Gellman |
| 8,597,170 B2 | 12/2013 | Walters et al. |
| 8,617,239 B2 | 12/2013 | Reitan |
| 8,672,868 B2 | 3/2014 | Simons |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,814,543 B2 | 8/2014 | Liebing |
| 8,814,776 B2 | 8/2014 | Hastie et al. |
| 8,814,933 B2 | 8/2014 | Siess |
| 8,827,887 B2 | 9/2014 | Curtis et al. |
| 8,849,398 B2 | 9/2014 | Evans |
| 8,864,642 B2 | 10/2014 | Scheckel |
| 8,888,728 B2 | 11/2014 | Aboul-Hosn et al. |
| 8,900,060 B2 | 12/2014 | Liebing |
| 8,926,492 B2 | 1/2015 | Scheckel |
| 8,932,141 B2 | 1/2015 | Liebing |
| 8,944,748 B2 | 2/2015 | Liebing |
| 8,979,493 B2 | 3/2015 | Roehn |

(56) References Cited

U.S. PATENT DOCUMENTS

| | | |
|---|---|---|
| 8,992,163 B2 | 3/2015 | McBride et al. |
| 8,998,792 B2 | 4/2015 | Scheckel |
| 9,028,216 B2 | 5/2015 | Schumacher et al. |
| 9,067,006 B2 | 6/2015 | Toellner |
| 9,072,825 B2 | 7/2015 | Pfeffer et al. |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,162,019 B2 | 10/2015 | Horvath et al. |
| 9,217,442 B2 | 12/2015 | Wiessler et al. |
| 9,259,521 B2 | 2/2016 | Simons |
| 9,278,189 B2 | 3/2016 | Corbett |
| 9,314,558 B2 | 4/2016 | Er |
| 9,327,067 B2 | 5/2016 | Zeng et al. |
| 9,328,741 B2 | 5/2016 | Liebing |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,592 B2 | 6/2016 | McBride et al. |
| 9,364,593 B2 | 6/2016 | McBride et al. |
| 9,370,613 B2 | 6/2016 | Hsu et al. |
| 9,381,288 B2 | 7/2016 | Schenck et al. |
| 9,393,384 B1 | 7/2016 | Kapur et al. |
| 9,402,942 B2 | 8/2016 | Hastie et al. |
| 9,404,505 B2 | 8/2016 | Scheckel |
| 9,416,783 B2 | 8/2016 | Schumacher et al. |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-Hosn et al. |
| 9,550,017 B2 | 1/2017 | Spanier et al. |
| 9,561,314 B2 | 2/2017 | Aboul-Hosn et al. |
| 9,572,915 B2 | 2/2017 | Heuring et al. |
| 9,597,205 B2 | 3/2017 | Tuval |
| 9,597,437 B2 | 3/2017 | Aboul-Hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,740 B2 | 6/2017 | Zeng et al. |
| 9,713,663 B2 | 7/2017 | Medvedev et al. |
| 9,717,833 B2 | 8/2017 | McBride et al. |
| 9,750,860 B2 | 9/2017 | Schumacher |
| 9,750,861 B2 | 9/2017 | Hastie et al. |
| 9,759,237 B2 | 9/2017 | Liebing |
| 9,764,113 B2 | 9/2017 | Tuval et al. |
| 9,771,801 B2 | 9/2017 | Schumacher et al. |
| 9,789,238 B2 | 10/2017 | Aboul-Hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,895,475 B2 | 2/2018 | Toellner et al. |
| 9,903,384 B2 | 2/2018 | Roehn |
| 9,907,890 B2 | 3/2018 | Muller |
| 9,907,891 B2 | 3/2018 | Wiessler et al. |
| 9,919,087 B2 | 3/2018 | Pfeffer et al. |
| 9,962,475 B2 | 5/2018 | Campbell et al. |
| 9,964,115 B2 | 5/2018 | Scheckel |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,419 B2 | 8/2018 | Er |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,107,299 B2 | 10/2018 | Scheckel |
| 10,117,980 B2 | 11/2018 | Keenan et al. |
| 10,119,550 B2 | 11/2018 | Bredenbreuker et al. |
| 10,149,932 B2 | 12/2018 | McBride et al. |
| 10,172,985 B2 | 1/2019 | Simon et al. |
| 10,179,197 B2 | 1/2019 | Kaiser et al. |
| 10,183,104 B2 | 1/2019 | Anderson et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | McBride et al. |
| 10,221,866 B2 | 3/2019 | Liebing |
| 10,231,838 B2 | 3/2019 | Chin et al. |
| 10,238,783 B2 | 3/2019 | Aboul-Hosn et al. |
| 10,245,363 B1 | 4/2019 | Rowe |
| 10,265,447 B2 | 4/2019 | Campbell et al. |
| 10,265,448 B2 | 4/2019 | Liebing |
| 10,279,095 B2 | 5/2019 | Aboul-Hosn et al. |
| 10,300,185 B2 | 5/2019 | Aboul-Hosn et al. |
| 10,300,186 B2 | 5/2019 | Aboul-Hosn et al. |
| 10,316,853 B2 | 6/2019 | Toellner |
| 10,330,101 B2 | 6/2019 | Toellner |
| 10,342,904 B2 | 7/2019 | Schumacher |
| 10,342,906 B2 | 7/2019 | D'Ambrosio et al. |
| 10,363,349 B2 | 7/2019 | Muller et al. |
| 10,369,260 B2 | 8/2019 | Smith et al. |
| 10,376,162 B2 | 8/2019 | Edelman et al. |
| 10,413,646 B2 | 9/2019 | Wiessler et al. |
| 10,449,276 B2 | 10/2019 | Pfeffer et al. |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,540 B2 | 11/2019 | Scheckel et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,857,272 B2 | 12/2020 | Liebing |
| 10,864,309 B2 | 12/2020 | McBride et al. |
| 10,865,801 B2 | 12/2020 | McBride et al. |
| 10,874,783 B2 | 12/2020 | Pfeffer et al. |
| 10,881,770 B2 | 1/2021 | Tuval et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 10,994,120 B2 | 5/2021 | Tuval et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,729 B2 | 6/2021 | Scheckel et al. |
| 11,040,187 B2 | 6/2021 | Wiessler et al. |
| RE48,649 E | 7/2021 | Siess |
| 11,077,294 B2 | 8/2021 | Keenan et al. |

(56) References Cited

U.S. PATENT DOCUMENTS

| | | |
|---|---|---|
| 11,116,960 B2 | 9/2021 | Simon et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,168,705 B2 | 11/2021 | Liebing |
| 11,185,680 B2 | 11/2021 | Tuval et al. |
| 11,191,944 B2 | 12/2021 | Tuval et al. |
| 11,197,690 B2 | 12/2021 | Fantuzzi et al. |
| 11,219,755 B2 | 1/2022 | Siess et al. |
| 11,229,786 B2 | 1/2022 | Zeng et al. |
| 11,253,692 B2 | 2/2022 | Schumacher |
| 11,253,693 B2 | 2/2022 | Pfeffer et al. |
| 11,260,212 B2 | 3/2022 | Tuval et al. |
| 11,260,215 B2 | 3/2022 | Scheckel et al. |
| 11,266,824 B2 | 3/2022 | Er |
| 11,268,521 B2 | 3/2022 | Toellner |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,291,825 B2 | 4/2022 | Tuval et al. |
| 11,298,525 B2 | 4/2022 | Jahangir |
| 11,305,105 B2 | 4/2022 | Corbett et al. |
| 11,313,228 B2 | 4/2022 | Schumacher et al. |
| 11,338,124 B2 | 5/2022 | Pfeffer et al. |
| 11,351,358 B2 | 6/2022 | Nix et al. |
| 11,364,373 B2 | 6/2022 | Corbett et al. |
| 11,421,701 B2 | 8/2022 | Schumacher et al. |
| 11,434,922 B2 | 9/2022 | Roehn |
| 2001/0041934 A1 | 11/2001 | Yamazaki et al. |
| 2002/0107536 A1 | 8/2002 | Hussein |
| 2002/0151799 A1 | 10/2002 | Pantages et al. |
| 2003/0055486 A1 | 3/2003 | Adams et al. |
| 2003/0088310 A1 | 5/2003 | Hansen et al. |
| 2003/0100816 A1 | 5/2003 | Siess |
| 2003/0149473 A1 | 8/2003 | Chouinard et al. |
| 2003/0208097 A1 | 11/2003 | Aboul-Hosn et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0167769 A1 | 6/2004 | Jassawalla et al. |
| 2004/0167415 A1 | 8/2004 | Gelfand et al. |
| 2004/0210236 A1 | 10/2004 | Allers et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0079274 A1 | 4/2005 | Palasis et al. |
| 2005/0085848 A1 | 4/2005 | Johnson et al. |
| 2005/0119682 A1 | 6/2005 | Nguyen et al. |
| 2005/0137680 A1 | 6/2005 | Ortiz et al. |
| 2005/0180854 A1 | 8/2005 | Grabau et al. |
| 2006/0062672 A1 | 3/2006 | McBride et al. |
| 2006/0064059 A1 | 3/2006 | Gelfand et al. |
| 2006/0106449 A1 | 5/2006 | Ben |
| 2006/0135961 A1 | 6/2006 | Rosenman et al. |
| 2006/0155322 A1 | 7/2006 | Sater et al. |
| 2006/0265051 A1 | 11/2006 | Caro et al. |
| 2007/0100415 A1 | 5/2007 | Licata et al. |
| 2007/0100435 A1 | 5/2007 | Case et al. |
| 2007/0142729 A1 | 6/2007 | Pfeiffer et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0282243 A1 | 12/2007 | Pini et al. |
| 2007/0293808 A1 | 12/2007 | Williams et al. |
| 2008/0009668 A1 | 1/2008 | Cohn |
| 2008/0103591 A1 | 5/2008 | Siess |
| 2008/0114339 A1 | 5/2008 | McBride et al. |
| 2008/0132747 A1 | 6/2008 | Shifflette |
| 2008/0132748 A1 | 6/2008 | Shifflette |
| 2008/0140189 A1 | 6/2008 | Nguyen et al. |
| 2008/0154236 A1 | 6/2008 | Elkins et al. |
| 2008/0183280 A1 | 7/2008 | Agnew et al. |
| 2008/0306327 A1 | 12/2008 | Shifflette |
| 2009/0024195 A1 | 1/2009 | Rezai et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0048793 A1 | 2/2010 | Baekelandt et al. |
| 2010/0049313 A1 | 2/2010 | Alon et al. |
| 2010/0130810 A1 | 5/2010 | Mohl |
| 2010/0152523 A1 | 6/2010 | MacDonald et al. |
| 2010/0268017 A1 | 10/2010 | Siess |
| 2011/0004046 A1 | 1/2011 | Campbell et al. |
| 2011/0034874 A1 | 2/2011 | Reitan et al. |
| 2011/0106244 A1 | 5/2011 | Ferrari et al. |
| 2011/0112567 A1 | 5/2011 | Lenker et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0282274 A1 | 11/2011 | Fulton |
| 2011/0301662 A1 | 12/2011 | Bar-Yoseph et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0089225 A1 | 4/2012 | Akkerman et al. |
| 2012/0116382 A1 | 5/2012 | Ku et al. |
| 2012/0130469 A1 | 5/2012 | Cragg et al. |
| 2012/0143141 A1 | 6/2012 | Verkaik et al. |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0245680 A1 | 9/2012 | Masuzawa et al. |
| 2012/0303112 A1 | 11/2012 | Armstrong et al. |
| 2012/0316586 A1 | 12/2012 | Demarais et al. |
| 2012/0328460 A1 | 12/2012 | Horvath et al. |
| 2013/0053623 A1 | 2/2013 | Evans et al. |
| 2013/0053732 A1 | 2/2013 | Heuser |
| 2013/0060077 A1 | 3/2013 | Liebing |
| 2013/0079874 A1 | 3/2013 | Doss et al. |
| 2013/0085318 A1 | 4/2013 | Toellner |
| 2013/0085319 A1 | 4/2013 | Evans et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2013/0245360 A1 | 9/2013 | Schumacher |
| 2013/0253328 A1 | 9/2013 | Zelenka et al. |
| 2013/0303831 A1 | 11/2013 | Evans |
| 2013/0303969 A1 | 11/2013 | Keenan et al. |
| 2014/0018840 A1 | 1/2014 | Morgan et al. |
| 2014/0025041 A1 | 1/2014 | Fukuoka et al. |
| 2014/0128659 A1 | 5/2014 | Heuring et al. |
| 2014/0255176 A1 | 9/2014 | Bredenbreuker et al. |
| 2014/0275720 A1 | 9/2014 | Ferrari |
| 2014/0275722 A1 | 9/2014 | Zimmermann et al. |
| 2014/0350523 A1 | 11/2014 | Dehdashtian et al. |
| 2015/0005570 A1 | 1/2015 | Fritz et al. |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0290372 A1* | 10/2015 | Muller ............... A61M 60/857 600/424 |
| 2015/0328382 A1 | 11/2015 | Corbett et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |

(56) References Cited

U.S. PATENT DOCUMENTS

| | | |
|---|---|---|
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0136343 A1 | 5/2016 | Anagnostopoulos |
| 2016/0144089 A1 | 5/2016 | Woo et al. |
| 2016/0184500 A1 | 6/2016 | Zeng |
| 2016/0256620 A1 | 9/2016 | Scheckel et al. |
| 2016/0279310 A1 | 9/2016 | Scheckel et al. |
| 2016/0331378 A1 | 11/2016 | Nitzan et al. |
| 2016/0354525 A1 | 12/2016 | McBride et al. |
| 2017/0007403 A1 | 1/2017 | Wildhirt et al. |
| 2017/0014562 A1 | 1/2017 | Liebing |
| 2017/0028115 A1 | 2/2017 | Muller |
| 2017/0035954 A1 | 2/2017 | Muller et al. |
| 2017/0049946 A1 | 2/2017 | Kapur et al. |
| 2017/0071769 A1 | 3/2017 | Mangiardi |
| 2017/0087286 A1 | 3/2017 | Spanier et al. |
| 2017/0087288 A1 | 3/2017 | Gross-Hardt et al. |
| 2017/0100527 A1 | 4/2017 | Schwammenthal et al. |
| 2017/0173237 A1 | 6/2017 | Pfeifer et al. |
| 2017/0197021 A1 | 7/2017 | Nitzan et al. |
| 2017/0215918 A1 | 8/2017 | Tao et al. |
| 2017/0232168 A1 | 8/2017 | Reichenbach et al. |
| 2017/0232171 A1 | 8/2017 | Roehn et al. |
| 2017/0290964 A1 | 10/2017 | Barry |
| 2017/0333067 A1 | 11/2017 | Wilson |
| 2017/0333607 A1 | 11/2017 | Zarins |
| 2017/0340791 A1 | 11/2017 | Aboul-Hosn et al. |
| 2017/0348470 A1 | 12/2017 | D'Ambrosio et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0303993 A1 | 10/2018 | Schwammenthal et al. |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0093769 A1 | 3/2019 | Lima Sarabanda et al. |
| 2019/0101130 A1 | 4/2019 | Bredenbreuker et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175802 A1 | 6/2019 | Tuval et al. |
| 2019/0175803 A1 | 6/2019 | Pfeffer et al. |
| 2019/0175805 A1 | 6/2019 | Tuval et al. |
| 2019/0175806 A1 | 6/2019 | Tuval et al. |
| 2019/0209753 A1 | 7/2019 | Tuval et al. |
| 2019/0209755 A1 | 7/2019 | Nix et al. |
| 2019/0209757 A1 | 7/2019 | Tuval et al. |
| 2019/0209758 A1 | 7/2019 | Tuval et al. |
| 2019/0211836 A1 | 7/2019 | Schumacher et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0290817 A1 | 9/2019 | Guo et al. |
| 2019/0307561 A1 | 10/2019 | Gosal et al. |
| 2019/0316591 A1 | 10/2019 | Toellner |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |
| 2019/0351118 A1 | 11/2019 | Graichen et al. |
| 2019/0365975 A1 | 12/2019 | Muller et al. |
| 2020/0038567 A1 | 2/2020 | Siess et al. |
| 2020/0078506 A1 | 3/2020 | Schwammenthal et al. |
| 2020/0087199 A1 | 3/2020 | Gimblet |
| 2020/0093973 A1 | 3/2020 | Gandhi et al. |
| 2020/0155739 A1 | 5/2020 | Siess et al. |
| 2020/0197585 A1 | 6/2020 | Scheckel et al. |
| 2020/0237981 A1 | 7/2020 | Tuval et al. |
| 2020/0237982 A1 | 7/2020 | Tuval et al. |
| 2020/0237984 A1 | 7/2020 | Tuval et al. |
| 2020/0237985 A1 | 7/2020 | Tuval et al. |
| 2020/0237986 A1 | 7/2020 | Tuval et al. |
| 2020/0246527 A1 | 8/2020 | Hildebrand et al. |
| 2020/0268952 A1 | 8/2020 | Nitzan et al. |
| 2020/0276369 A1 | 9/2020 | Nitzan et al. |
| 2020/0288988 A1 | 9/2020 | Goldvasser |
| 2020/0405926 A1 | 12/2020 | Alexander et al. |
| 2021/0023285 A1 | 1/2021 | Brandt |
| 2021/0023286 A1 | 1/2021 | Tuval et al. |
| 2021/0069394 A1 | 3/2021 | Tuval et al. |
| 2021/0069395 A1 | 3/2021 | Tuval et al. |
| 2021/0077692 A1 | 3/2021 | Tanner et al. |
| 2021/0145475 A1 | 5/2021 | Tao et al. |
| 2021/0170081 A1 | 6/2021 | Kanz |
| 2021/0178145 A1 | 6/2021 | Tuval et al. |
| 2021/0236797 A1 | 8/2021 | D'Ambrosio et al. |
| 2021/0299433 A1 | 9/2021 | Siess et al. |
| 2022/0072297 A1 | 3/2022 | Tuval et al. |
| 2022/0079457 A1 | 3/2022 | Tuval et al. |
| 2022/0088368 A1 | 3/2022 | Tuval et al. |
| 2022/0134085 A1 | 5/2022 | Siess et al. |
| 2022/0184376 A1 | 6/2022 | Tuval et al. |
| 2022/0226632 A1 | 7/2022 | Tuval et al. |
| 2023/0071248 A1 | 3/2023 | Keenan et al. |
| 2023/0137473 A1 | 5/2023 | Zipory et al. |
| 2023/0226342 A1 | 7/2023 | Tuval et al. |

FOREIGN PATENT DOCUMENTS

| | | |
|---|---|---|
| CA | 2927346 A1 | 4/2009 |
| CN | 101448535 A | 6/2009 |
| CN | 102805885 A | 12/2012 |
| CN | 113457006 A | 10/2021 |
| DE | 1033690 B | 7/1958 |
| DE | 10336902 B3 | 8/2004 |
| EP | 0916359 A1 | 5/1999 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |

(56) References Cited

FOREIGN PATENT DOCUMENTS

| | | |
|---|---|---|
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 1207934 B1 | 8/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3115070 A1 | 1/2017 |
| EP | 3127562 A1 | 2/2017 |
| EP | 2922486 B1 | 5/2017 |
| EP | 3216467 A1 | 9/2017 |
| EP | 3222302 A1 | 9/2017 |
| EP | 3236079 A1 | 10/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3545983 A1 | 10/2019 |
| EP | 3606575 A1 | 2/2020 |
| EP | 3737436 A1 | 11/2020 |
| EP | 3858421 A1 | 8/2021 |
| EP | 3897814 A1 | 10/2021 |
| EP | 4218899 A1 | 8/2023 |
| GB | 2451161 A | 1/2009 |
| GB | 2504175 A | 1/2014 |
| GB | 2504177 A | 1/2014 |
| JP | 2003504091 A | 2/2003 |
| JP | 2009530041 A | 8/2009 |
| JP | 2012505038 A | 3/2012 |
| JP | 2012527269 A | 11/2012 |
| JP | 2016509950 A | 4/2016 |
| JP | 2018535727 A | 12/2018 |
| WO | 9001972 A1 | 3/1990 |
| WO | 90/13321 | 11/1990 |
| WO | 1994/01148 A1 | 1/1994 |
| WO | 99/34847 | 7/1999 |
| WO | 2001/083016 A2 | 5/2000 |
| WO | 2000043053 A1 | 7/2000 |
| WO | 0062838 A2 | 10/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007081818 A2 | 7/2007 |
| WO | 2007112033 A2 | 10/2007 |
| WO | 2007127477 A2 | 11/2007 |
| WO | 2008005747 A2 | 1/2008 |
| WO | 2008005990 A2 | 1/2008 |
| WO | 2008055301 A1 | 5/2008 |
| WO | 2008104858 A2 | 9/2008 |
| WO | 2009010963 A2 | 1/2009 |
| WO | 2009046096 A1 | 4/2009 |
| WO | 2009129481 A1 | 10/2009 |
| WO | 2010042546 | 4/2010 |
| WO | 2010063494 A1 | 6/2010 |
| WO | 2010105854 A1 | 9/2010 |
| WO | 2010127871 A1 | 11/2010 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2011089022 A1 | 7/2011 |
| WO | 2012007141 A1 | 1/2012 |
| WO | 2012094535 A2 | 7/2012 |
| WO | 2013032849 A1 | 3/2013 |
| WO | 2013070186 A1 | 5/2013 |
| WO | 2013093001 A2 | 6/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015160943 A1 | 10/2015 |
| WO | 2015177793 A2 | 11/2015 |
| WO | 2016001218 A1 | 1/2016 |
| WO | 2016005803 A2 | 1/2016 |
| WO | 2016185473 A1 | 11/2016 |
| WO | 2016207293 A1 | 12/2016 |
| WO | 2017053361 A1 | 3/2017 |
| WO | 2017060254 A1 | 4/2017 |
| WO | 2017081561 A1 | 5/2017 |
| WO | 2017137604 A1 | 8/2017 |
| WO | 2017147291 A1 | 8/2017 |
| WO | 2018033920 A1 | 2/2018 |
| WO | 2018061001 A2 | 4/2018 |
| WO | 2018061002 A1 | 4/2018 |
| WO | 2018067410 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2018226991 A1 | 12/2018 |
| WO | 2018234454 A1 | 12/2018 |
| WO | 2019094963 A1 | 5/2019 |
| WO | 2019125899 A1 | 6/2019 |
| WO | 2019138350 A2 | 7/2019 |
| WO | 2019152875 A1 | 8/2019 |
| WO | 2019158996 A1 | 8/2019 |
| WO | 2019229223 A1 | 12/2019 |
| WO | 2020152611 A2 | 7/2020 |
| WO | 2021152012 A1 | 8/2021 |
| WO | 2021159147 A1 | 8/2021 |
| WO | 2021198881 A1 | 10/2021 |
| WO | 2021205346 A2 | 10/2021 |
| WO | 2022189932 A1 | 9/2022 |
| WO | 2023062453 A1 | 4/2023 |
| WO | 2024057252 A1 | 3/2024 |
| WO | 2024057253 A2 | 3/2024 |
| WO | 2024057254 A1 | 3/2024 |
| WO | 2024057255 A2 | 3/2024 |
| WO | 2024057256 A2 | 3/2024 |
| WO | 2024057257 A2 | 3/2024 |

OTHER PUBLICATIONS

Corrected Notice of Allowability for U.S. Appl. No. 16/810,172 mailed Feb. 2, 2022.
Examination Report for Australian Patent Application No. 2017349920 issued on Jun. 2, 2022.
Examination Report for Indian Patent Application No. 202047017397 issued on May 4, 2022.
Extended European Search Report for European Application No. 21208803.3 issued on Apr. 13, 2022.

(56) References Cited

OTHER PUBLICATIONS

Extended European Search Report for European Application No. 21209256.3 issued on Mar. 2, 2022.
Final Office Action for U.S. Appl. No. 16/275,559 mailed May 17, 2022.
Final Office Action for U.S. Appl. No. 17/069,064 mailed May 25, 2022.
Issue Notification for U.S. Appl. No. 16/276,965 mailed Mar. 16, 2022.
Issue Notification for U.S. Appl. No. 16/277,411 mailed Feb. 9, 2022.
Issue Notification for U.S. Appl. No. 16/810,086 mailed Mar. 9, 2022.
Issue Notification for U.S. Appl. No. 16/810,172 mailed Mar. 23, 2022.
Issue Notification for U.S. Appl. No. 17/069,321 mailed Mar. 16, 2022.
Non-Final Office Action for U.S. Appl. No. 16/275,559 mailed Jan. 26, 2022.
Non-Final Office Action for U.S. Appl. No. 16/810,121 mailed Mar. 9, 2022.
Non-Final Office Action for U.S. Appl. No. 17/176,344 mailed Apr. 20, 2022.
Notice of Allowance for U.S. Appl. No. 16/276,965 mailed Jan. 26, 2022.
Notice of Allowance for U.S. Appl. No. 16/810,121 mailed Jun. 1, 2022.
Notice of Allowance for U.S. Appl. No. 16/810,270 mailed Apr. 14, 2022.
Notice of Allowance for U.S. Appl. No. 17/069,321 mailed Feb. 2, 2022.
Restriction Requirement for U.S. Appl. No. 16/810,116 mailed Jun. 29, 2022.
Supplemental Notice of Allowability for U.S. Appl. No. 16/276,965 mailed Mar. 10, 2022.
Supplemental Notice of Allowability for U.S. Appl. No. 16/276,965 mailed Mar. 2, 2022.
U.S. Appl. No. 16/810,086, filed Mar. 5, 2020.
U.S. Appl. No. 16/810,121, filed Mar. 5, 2020.
U.S. Appl. No. 17/528,015, filed Nov. 16, 2021.
U.S. Appl. No. 17/528,807, filed Nov. 17, 2021.
U.S. Appl. No. 17/532,318, filed Nov. 22, 2021.
U.S. Appl. No. 17/677,571, filed Feb. 22, 2022.
U.S. Appl. No. 17/678,122, filed Feb. 23, 2022.
U.S. Appl. No. 17/857,402, filed Jul. 5, 2022.
Corrected Notice of Allowability for U.S. Appl. No. 16/279,352 mailed Nov. 3, 2021.
Corrected Notice of Allowability for U.S. Appl. No. 16/281,237 mailed Mar. 31, 2021.
Examination Report for Indian Patent Application No. 201917018651 mailed Jun. 30, 2021.
Extended Search Report for European Application No. 19172327.9 mailed Aug. 23, 2019.
Extended Search Report for European Application No. 20159714.3 mailed Jul. 3, 2020.
Extended Search Report for European Application No. 20159716.8 mailed Jul. 3, 2020.
Extended Search Report for European Application No. 20159718.4 mailed Jul. 9, 2020.
Extended Search Report for European Application No. 20195082.1 mailed Nov. 5, 2020.
Extended Search Report for European Application No. 20195084.7 mailed Nov. 5, 2020.
Extended Search Report for European Application No. 20195085.4 mailed Nov. 4, 2020.
Extended Search Report for European Application No. 20195987.1 mailed Nov. 5, 2020.
Extended Search Report for European Application No. 21156647.6 mailed May 21, 2021.
Extended Search Report for European Application No. 21158196.2 mailed Apr. 8, 2021.
Extended Search Report for European Application No. 21158902.3 mailed Apr. 29, 2021.
Extended Search Report for European Application No. 21158903.1 mailed Apr. 9, 2021.
Final Office Action for U.S. Appl. No. 16/275,559 mailed Jan. 4, 2021.
Final Office Action for U.S. Appl. No. 16/275,559 mailed Oct. 20, 2021.
Final Office Action for U.S. Appl. No. 16/276,965 mailed Apr. 13, 2021.
Final Office Action for U.S. Appl. No. 16/277,411 mailed Jun. 21, 2021.
Final Office Action for U.S. Appl. No. 16/279,352 mailed May 3, 2021.
International Search Report and Written Opinion from International Application No. PCT/IB2020/050515 mailed Sep. 9, 2020.
International Search Report and Written Opinion from International Application No. PCT/IB2021/052590 mailed Sep. 14, 2021.
International Search Report and Written Opinion from International Application No. PCT/IB2021/052857 mailed Oct. 5, 2021.
International Search Report and Written Opinion from International Application No. PCT/IL2017/051158 mailed Jan. 17, 2018.
International Search Report and Written Opinion from International Application No. PT/IB2019/050186 mailed Jul. 18, 2019.
Invitation to Pay Additional Fees for International Application No. PCT/IB2020/050515 mailed Mar. 31, 2020.
Invitation to Pay Additional Fees for International Application No. PCT/IB2021/052590 mailed Jul. 23, 2021.
Invitation to Pay Additional Fees for International Application No. PCT/IB2021/052857 mailed Jul. 7, 2021.
Issue Notification for U.S. Appl. No. 16/278,482 mailed Jan. 13, 2021.
Issue Notification for U.S. Appl. No. 16/279,352 mailed Nov. 10, 2021.
Issue Notification for U.S. Appl. No. 16/280,566 mailed Nov. 10, 2021.
Issue Notification for U.S. Appl. No. 16/281,237 mailed Apr. 14, 2021.
Issue Notification for U.S. Appl. No. 16/281,264 mailed Dec. 16, 2020.
Issue Notification for U.S. Appl. No. 16/750,354 mailed Nov. 17, 2021.
Non-Final Office Action for U.S. Appl. No. 16/275,559 mailed May 26, 2021.
Non-Final Office Action for U.S. Appl. No. 16/275,559 mailed Sep. 4, 2020.
Non-Final Office Action for U.S. Appl. No. 16/276,965 mailed Jul. 26, 2021.
Non-Final Office Action for U.S. Appl. No. 16/276,965 mailed Jun. 19, 2020.
Non-Final Office Action for U.S. Appl. No. 16/276,965 mailed Nov. 30, 2020.
Non-Final Office Action for U.S. Appl. No. 16/277,411 mailed Feb. 9, 2021.
Non-Final Office Action for U.S. Appl. No. 16/278,482 mailed Jun. 23, 2020.
Non-Final Office Action for U.S. Appl. No. 16/279,352 mailed Nov. 10, 2020.
Non-Final Office Action for U.S. Appl. No. 16/280,566 mailed Dec. 21, 2020.
Non-Final Office Action for U.S. Appl. No. 16/281,237 mailed Aug. 21, 2020.
Non-Final Office Action for U.S. Appl. No. 16/281,264 mailed Jun. 29, 2020.
Non-Final Office Action for U.S. Appl. No. 17/069,064 mailed Dec. 9, 2021.
Non-Final Office Action for U.S. Appl. No. 17/069,321 mailed Nov. 18, 2021.
Notice of Allowance for U.S. Appl. No. 16/277,411 mailed Dec. 8, 2021.

(56) References Cited

OTHER PUBLICATIONS

Notice of Allowance for U.S. Appl. No. 16/278,482 mailed Dec. 2, 2020.
Notice of Allowance for U.S. Appl. No. 16/279,352 mailed Oct. 1, 2021.
Notice of Allowance for U.S. Appl. No. 16/280,566 mailed Aug. 31, 2021.
Notice of Allowance for U.S. Appl. No. 16/281,237 mailed Feb. 1, 2021.
Notice of Allowance for U.S. Appl. No. 16/281,264 mailed Nov. 12, 2020.
Notice of Allowance for U.S. Appl. No. 16/750,354 mailed Oct. 18, 2021.
Notice of Allowance for U.S. Appl. No. 16/810,086 mailed Jan. 7, 2022.
Notice of Allowance for U.S. Appl. No. 16/810,172 mailed Jan. 10, 2022.
Office Action for Chinese Application No. 201780066201.3 mailed Jun. 29, 2021.
Office Action for Japanese Patent Application No. 2019-521643 mailed Sep. 28, 2021.
Restriction Requirement for U.S. Appl. No. 16/275,559 mailed Jun. 2, 2020.
Restriction Requirement for U.S. Appl. No. 16/279,352 mailed Aug. 11, 2020.
Restriction Requirement for U.S. Appl. No. 16/280,566 mailed Aug. 11, 2020.
Supplemental Notice of Allowability for U.S. Appl. No. 16/278,482 mailed Dec. 24, 2020.
Supplemental Notice of Allowability for U.S. Appl. No. 16/279,352 mailed Oct. 21, 2021.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,237, filed Feb. 21, 2019.
U.S. Appl. No. 16/281,264, filed Feb. 21, 2019.
U.S. Appl. No. 16/750,354, filed Jan. 23, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.
U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
U.S. Appl. No. 17/176,344, filed Feb. 16, 2021.
U.S. Appl. No. 17/177,296, filed Feb. 17, 2021.
U.S. Appl. No. 17/180,041, filed Feb. 19, 2021.
U.S. Appl. No. 17/182,482, filed Feb. 23, 2021.
U.S. Appl. No. 17/609,589, filed Nov. 8, 2021.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
U.S. Application No. 63/006, 122 filed Apr. 7, 2020.
U.S. Appl. No. 63/114,136, filed Nov. 16, 2020.
U.S. Appl. No. 63/129,983, filed Dec. 23, 2020.
"Translation of decision of Board 4 (Nullity Board) of the German Federal Patent Court re German patent 10336902", pronounced Nov. 15, 2016, and appendices to decision, 62 pages.
Agarwal , et al., "Newer-generation ventricular assist devices.", Best Practice & Research Clinical Anaesthesiology, 2012, pp. 117-130.
Alba , et al., "The future is here: ventricular assist devices for the failing heart", Expert review of cardiovascular therapy, 2009, pp. 1067-1077.
Bai , et al., "A Split-Array, C-2C Switched-Capacitor Power Amplifier in 65 nm CMOS", IEEE Radio Frequency Integrated Circuits Symposium, 2017, pp. 336-339.
Burnett , et al., "Renal Interstitial Pressure And Sodium Excretion During Renal Vein Constriction", American Physiological Society, 1980, pp. F279-F282.
Cassidy , et al., "The Conductance vol. Catheter Technique for Measurement of Left Ventricular vol. in Young Piglets", Pediatric Research, 1992, pp. 85-90.
Coxworth , "Artificial Vein Valve Could Replace Drugs For Treating Common Circulatory Problem", Published on Gizmag website (http://www.gizmag.com/artificial-venous-valve-cvi/21785/), Mar. 9, 2012.
Damman , et al., "Decreased Cardiac Output, Venous Congestion And The Association With Renal Impairment In Patients With Cardiac Dysfunction", European Journal of Heart Failure, 2007, pp. 872-878.
Damman , et al., "Increased Central Venous Pressure Is Associated With Impaired Renal Function And Mortality In A Broad Spectrum Of Patients With Cardiovascular Disease", Journal of American College of Cardiology, 2009, pp. 582-588.
Doty , et al., "The Effect Of Increased Renal Venous Pressure On Renal Function", The Journal of Trauma,, Dec. 1999, pp. 1000-1003.
Felker , et al., "Anemia As A Risk Factor And Therapeutic Target In Heart Failure", Journal of the American College of Cardiology, 2004, pp. 959-966.
Firth , et al., "Raised Venous Pressure: A Direct Cause Of Sodium Retention In Oedema?", The Lancet, May 7, 1988, pp. 1033-1036.
Forman , et al., "Incidence, Predictors At Admission, And Impact Of Worsening Renal Function Among Patients Hospitalized With Heart Failure", Journal of American College of Cardiology, 2004, pp. 61-67.
Fraser , et al., "The use of computational fluid dynamics in the development of ventricular assist devices", Medical engineering & physics, 2011, pp. 263-280.
Frazier , et al., "First Human Use of the Hemopump, a Catheter Mounted Ventricular Assist Device", Ann Thorac Surg, 1990, pp. 299-304.
Gomes , et al., "Heterologous Valve Implantation In The Infra-Renal Vena Cava For Treatment Of The Iliac Venous Valve Regurgitation Disease: Experimental Study", Rev Bras Cir Cardiovasc, 2002, pp. 367-369.
Haddy , et al., "Effect Of Elevation Of Intraluminal Pressure On Renal Vascular Resistance", Circulation Research Journal Of The American Heart Association, 1956, pp. 659-663.
Heywood , et al., "High Prevalence Of Renal Dysfunction And Its Impact On Outcome In 118,465 Patients Hospitalized With Acute Decompensated Heart Failure: A Report From The ADHERE Database", Journal of Cardiac Failure, 2007, pp. 422-430.
Hillege , et al., "Renal Function As A Predictor Of Outcome In A Broad Spectrum Of Patients With Heart Failure", Circulation Journal of the American Heart Association, 2006, pp. 671-678.
Hillege , et al., "Renal Function, Neurohormonal Activation, And Survival In Patients With Chronic Heart Failure", Circulation Journal of the American Heart Association, 2000, pp. 203-210.

(56) References Cited

OTHER PUBLICATIONS

Hsu, et al., "Review of recent patents on foldable ventricular assist devices", Recent Patents on Biomedical Engineering, 2012, pp. 208-222.

Ikari, "The Physics Of Guiding Catheter; The IKARI Guiding Catheter In TRI", available at httu:i /www.docstoc.com/docs/148136553/The-[KARI-catheter---anovel-guide-for-TRI--.

Kafagy, et al., "Design of axial blood pumps for patients with dysfunctional fontan physiology: computational studies and performance testing", Artificial organs, 2015, pp. 34-42.

Kang, et al., "Fluid dynamics aspects of miniaturized axial-flow blood pump", Bio-medical materials and engineering, 2014, pp. 723-729.

Koochaki, et al., "A new design and computational fluid dynamics study of an implantable axial blood pump", Australasian Physical & Engineering Sciences in Medicine, 2013, pp. 417-422.

Lauten, et al., "Heterotopic Transcatheter Tricuspid Valve Implantation: First-In-Man Application Of A Novel Approach To Tricuspid Regurgitation", European Heart Journal, Feb. 15, 2011, pp. 1207-1213.

McAlister, et al., "Renal Insufficiency And Heart Failure: Prognostic And Therapeutic Implications From A Prospective Cohort Study", Circulation Journal of the American Heart Association, 2004, pp. 1004-1009.

Meyns, et al., "The Heart-Hemopump Interaction: A Study of Hemopump Flow as a Function of Cardiac Activity", Artificial Organs, 1996, pp. 641-649.

Mullens, et al., "Elevated Intra-Abdominal Pressure In Acute Decompensated Heart Failure. A Potential Contributor To Worsening Renal Function", Journal of the American College of Cardiology, 2008, pp. 300-306.

Mullens, et al., "Importance Of Venous Congestion For Worsening Of Renal Function In Advanced Decompensated Heart Failure", Journal of American College of Cardiology, 2009, pp. 589-596.

Mullens, et al., "Prompt Reduction In Intra-Abdominal Pressure Following Large-Volume Mechanical Fluid Removal Improves Renal Insufficiency In Refractory Decompensated Heart Failure", Journal of Cardiac Failure, 2008, pp. 508-514.

Notarius, et al., "Central Venous Pressure During Exercise: Role Of Muscle Pump", Canadian Journal of Physiology and Pharmacology, 1996, pp. 647-651.

Park, et al., "Nutcracker Syndrome: Intravascular Stenting Approach", Nephrol Dial Transplant, 2000, pp. 99-101.

Reul, et al., "Blood pumps for circulatory support", Perfusion-Sevenoaks, 2000, pp. 295-312.

Reul, et al., "Rotary blood pumps in circulatory assist", Perfusion, May 1995, pp. 153-158.

Rodefeld, "Cavopulmonary assist for the univentricular Fontan circulation: von Karman viscous impeller pump", The Journal of Thoracic and Cardiovascular Surgery, 2010, pp. 529-536.

Schmitz-Rode, et al., "An Expandable Percutaneous Catheter Pump For Left Ventricular Support", Journal of the American College of Cardiology, 2005, pp. 1856-1861.

Schmitz-Rode, et al., "Axial flow catheter pump for circulatory support", Biomed Tech (Berl), 2002, pp. 142-143.

Semple, et al., "Effect Of Increased Renal Venous Pressure On Circulatory "Autoregulation" Of Isolated Dog Kidneys", Circulation Research Journal of The American Heart Association, 1959, pp. 643-648.

Sianos, et al., "The Recover® LP 2.5 catheter-mounted left ventricular assist device", EuroIntervention, 2006, pp. 116-119.

Siess, et al., "Concept, realization, and first in vitro testing of an intraarterial microaxial blood pump", Artificial Organs, 1995, pp. 644-652.

Siess, et al., "Hemodynamic system analysis of intraarterial microaxial pumps in vitro and in vivo", Artificial Organs, Jun. 1996, pp. 650-661.

Siess, "PhD Chapter 3—English translation", https://www.shaker.eu/en/content/catalogue/index.asp?lang=en&ID=8&ISBN=978-3-8265-6150-4&search=yes.

Song, et al., "Axial flow blood pumps", ASAIO journal, 2003, pp. 355-364.

Tang, et al., "Anemia In Chronic Heart Failure: Prevalence, Etiology, Clinical Correlates, And Treatment Options", Circulation Journal of the American Heart Association, 2006, pp. 2454-2461.

Throckmorton, et al., "Design of a protective cage for an intravascular axial flow blood pump to mechanically assist the failing Fontan", Artificial organs, 2009, pp. 611-621.

Throckmorton, et al., "Mechanical Cavopulmonary Assist for the Univentricular Fontan Circulation Using a Novel Folding Propeller Blood Pump", ASAIO Journal, 2007, pp. 734-741.

Thunberg, et al., "Ventricular assist devices today and tomorrow", Journal of cardiothoracic and vascular anesthesia, 2010, pp. 656-680.

Timms, "A review of clinical ventricular assist devices", Medical engineering & physics, 2011, pp. 1041-1047.

Triep, et al., "Computational Fluid Dynamics and Digital Particle Image Velocimetry Study of the Flow Through an Optimized Micro-axial Blood Pump", Artificial Organs, May 2006, pp. 384-391.

Uthoff, et al., "Central venous pressure at emergency room presentation predicts cardiac rehospitalization in patients with decompensated heart failure", European Journal of Heart Failure, 2010, pp. 469-476.

Van Mieghem, et al., "Design and Principle of Operation of the HeartMate PHPTM (Percutaneous Heart Pump)", EuroIntervention, 2016.

Vercaemst, et al., "Impella: A Miniaturized Cardiac Support System in an Era of Minimal Invasive Cardiac Surgery", Presented at the 39th International Conference of the American Society of Extra-Corporeal Technology, Mar. 22-25, 2001.

Wampler, "The first co-axial flow pump for human use: the Hemopump", Flameng W. (eds) Temporary Cardiac Assist with an Axial Pump System, 1991.

Wencker, "Acute Cardio-Renal Syndrome: Progression From Congestive Heart Failure To Congestive Kidney Failure", Current Heart Failure Reports, 2007, pp. 134-138.

Winton, "The Control Of Glomerular Pressure By Vascular Changes Within The Mammalian Kidney, Demonstrated By The Actions Of Adrenaline", Journal of Physiology, Nov. 1931, pp. 151-162.

Winton, "The Influence Of Venous Pressure On The Isolated Mammalian Kidney", Journal of Physiology, Jun. 6, 1931, pp. 49-61.

Wood, "The Mechanism Of The Increased Venous Pressure With Exercise In Congestive Heart Failure", Journal of Clinical Investigation, 1962, pp. 2020-2024.

Wu, et al., "Design and simulation of axial flow maglev blood pump", International Journal of Information Engineering and Electronic Business, 2011, p. 42.

Yancy, et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, 2006, pp. 76-84.

Wampler, et al., "Treatment of Cardiogenic Shock With the Hemopump Left Ventricular Assist Device", Annual of Thoracic Surgery, vol. 52, pp. 560-513, 1991.

Wampler, "U.S. News & World Report", Captain Hemo, pp. 1-2, May 16, 1988.

Corrected Notice of Allowability for U.S. Appl. No. 16/810,121 mailed Sep. 20, 2022.

Corrected Notice of Allowability for U.S. Appl. No. 17/182,482 mailed Feb. 7, 2023.

Examination Report for Australian Patent Application No. 2017349920 mailed Nov. 4, 2022.

Extended European Search Report for European Application No. 22155936.2 mailed Jul. 8, 2022.

Extended European Search Report for European Application No. 22163648.3 mailed Aug. 10, 2022.

Extended European Search Report for European Application No. 22163653.3 mailed Jul. 1, 2022.

(56) References Cited

OTHER PUBLICATIONS

Final Office Action for U.S. Appl. No. 17/176,344 mailed Oct. 12, 2022.
International Search Report and Written Opinion from International Application No. PCT/IB2022/051990 mailed Aug. 10, 2022.
Invitation to Pay Additional Fees for International Application No. PCT/IB2022/051990 mailed May 13, 2022.
Issue Notification for U.S. Appl. No. 16/810,270 mailed Oct. 12, 2022.
Non-Final Office Action for U.S. Appl. No. 16/275,559 mailed Jan. 19, 2023.
Non-Final Office Action for U.S. Appl. No. 16/952,327 mailed Nov. 8, 2022.
Non-Final Office Action for U.S. Appl. No. 16/952,389 mailed Dec. 21, 2022.
Non-Final Office Action for U.S. Appl. No. 16/952,444 mailed Jan. 6, 2023.
Non-Final Office Action for U.S. Appl. No. 17/069,064 mailed Nov. 7, 2022.
Non-Final Office Action for U.S. Appl. No. 17/069,570 mailed Oct. 6, 2022.
Non-Final Office Action for U.S. Appl. No. 17/070,323 mailed Oct. 6, 2022.
Non-Final Office Action for U.S. Appl. No. 17/070,670 mailed Oct. 5, 2022.
Non-Final Office Action for U.S. Appl. No. 17/077,769 mailed Oct. 5, 2022.
Non-Final Office Action for U.S. Appl. No. 17/180,041 mailed Jan. 31, 2023.
Notice of Allowance for U.S. Appl. No. 16/810,121 mailed Aug. 19, 2022.
Notice of Allowance for U.S. Appl. No. 16/810,270 mailed Jul. 22, 2022.
Notice of Allowance for U.S. Appl. No. 17/182,482 mailed Jan. 5, 2023.
Office Action for Japanese Application No. 2019-521643 mailed May 10, 2022.
Office Action for Japanese Application No. 2019-521643 mailed Oct. 27, 2022.
Third Party Submission received during the prosecution of U.S. Appl. No. 17/078,439, filed Sep. 28, 2022.
U.S. Appl. No. 63/003,955, filed Apr. 2, 2020.
U.S. Appl. No. 63/158,708, filed Mar. 9, 2021.
U.S. Appl. No. 63/254,321, filed Oct. 11, 2021.
"Compendium of Technical and Scientific Information for the Hemopump Temporary Cardiac Assist System", Johnson & Johnson Interventional Systems, 1988, pp. 1-15.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Butler, et al., "The Hemopump—A New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Dekker, et al., "Efficacy of a New Intraaortic Propeller Pump vs the Intraaortic Balloon Pump", Chest, vol. 123, Issue 6, Jun. 2003, pp. 2089-2095.
Flameng, "Temporary Cardiac Assist with an Axial Pump System", Steinkopff Verlag Darmstadt, 1991, 79 pages.
Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gunther, et al., "Experimentelle Radiologie", Life Sciences, Berichte Aus Der Rheinischwestfälischen Technischen Hochschule Aachen Ausgabe Feb. 2002, 9 pages.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Roundtree, et al., "The Hemopump Cardiac Assist System: Nursing Care of the Patient", Reprinted from Critical Care Nurse, Apr. 1991.
Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.
Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.
Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Extended European Search Report for EP Patent Application No. 22163640.0 mailed Jun. 29, 2022.
Extended Search Report for European Application No. 23189147.4 mailed Dec. 13, 2023.
Extended Search Report for European Application No. 23189148.2 mailed Dec. 13, 2023.
Extended Search Report for European Application No. 23189149.0 mailed Dec. 13, 2023.
Hearing Notice for Indian Patent Application No. 201917018651 mailed Dec. 11, 2023.
Non-Final Office Action for U.S. Appl. No. 17/528,807 mailed Jan. 12, 2024.
Office Action for Canadian Application No. 3,176,272 mailed Jan. 2, 2024.
Office Action for Chinese Application No. 202080017728.9 mailed Nov. 6, 2023.
Corrected Notice of Allowability for U.S. Appl. No. 16/810,116 mailed Apr. 7, 2023.
Corrected Notice of Allowability for U.S. Appl. No. 17/070,323 mailed Jun. 1, 2023.
Corrected Notice of Allowability for U.S. Appl. No. 17/180,041 mailed Jun. 30, 2023.
Examination Report for Indian Patent Application No. 202147033522 mailed May 24, 2023.
Extended Search Report and Preliminary Opinion for European Application No. 23159720.4 mailed Jun. 27, 2023.
Extended Search Report for European Application No. 22197511.3 mailed Dec. 5, 2022.
Extended Search Report for European Application No. 23159721.2 mailed Jun. 26, 2023.
Extended Search Report for European Application No. 23159724.6 mailed Jun. 26, 2023.

(56) References Cited

OTHER PUBLICATIONS

Extended Search Report for European Application No. 23159725.3 mailed Jun. 28, 2023.
Final Office Action for U.S. Appl. No. 16/952,327 mailed Jun. 8, 2023.
Final Office Action for U.S. Appl. No. 16/952,389 mailed Jul. 18, 2023.
Final Office Action for U.S. Appl. No. 16/952,444 mailed Jul. 5, 2023.
Final Office Action for U.S. Appl. No. 17/069,570 mailed Apr. 28, 2023.
Final Office Action for U.S. Appl. No. 17/070,670 mailed Jun. 2, 2023.
Final Office Action for U.S. Appl. No. 17/077,769 mailed Jun. 7, 2023.
International Search Report and Written Opinion from International Application No. PCT/IB2022/058101 mailed Feb. 20, 2023.
Issue Notification for U.S. Appl. No. 16/810,116 mailed May 17, 2023.
Non-Final Office Action for U.S. Appl. No. 17/078,439 mailed Jun. 1, 2023.
Non-Final Office Action for U.S. Appl. No. 17/078,472 mailed May 4, 2023.
Notice of Allowance for U.S. Appl. No. 16/275,559 mailed Jul. 27, 2023.
Notice of Allowance for U.S. Appl. No. 16/810,116 mailed Mar. 13, 2023.
Notice of Allowance for U.S. Appl. No. 17/069,064 mailed Mar. 8, 2023.
Notice of Allowance for U.S. Appl. No. 17/070,323 mailed Aug. 30, 2023.
Notice of Allowance for U.S. Appl. No. 17/070,323 mailed May 15, 2023.
Notice of Allowance for U.S. Appl. No. 17/173,944 mailed Jul. 10, 2023.
Notice of Allowance for U.S. Appl. No. 17/180,041 mailed Jun. 13, 2023.
Notice of Allowance for U.S. Appl. No. 17/180,041 mailed Sep. 18, 2023.
Notice of Allowance for U.S. Appl. No. 17/182,482 mailed Apr. 21, 2023.
Office Action for Canadian Application No. 3,039,285 mailed Mar. 24, 2023.
Office Action for Canadian Application No. 3,080,800 mailed Sep. 12, 2023.
Office Action for Canadian Application No. 3,122,415 mailed Mar. 31, 2023.
Office Action for Chinese Application No. 201980007116.9 mailed Nov. 28, 2022.
Office Action for Japanese Application No. 2019-521643 mailed Apr. 11, 2023.
Office Action for Japanese Application No. 2020-537746 mailed Feb. 21, 2023.
U.S. Appl. No. 18/121,995, filed Mar. 15, 2023.
U.S. Appl. No. 18/122,456, filed Mar. 16, 2023.
U.S. Appl. No. 18/122,486, filed Mar. 16, 2023.
U.S. Appl. No. 18/122,504, filed Mar. 16, 2023.
U.S. Appl. No. 18/447,025, filed Aug. 9, 2023.
U.S. Appl. No. 18/447,050, filed Aug. 9, 2023.
U.S. Appl. No. 18/447,064, filed Aug. 9, 2023.
U.S. Appl. No. 18/447,074, filed Aug. 9, 2023.
U.S. Appl. No. 18/447,086, filed Aug. 9, 2023.
U.S. Appl. No. 63/317,199, filed Mar. 7, 2022.
Corrected Notice of Allowance for U.S. Appl. No. 16/275,559 mailed Nov. 8, 2023.
Corrected Notice of Allowance for U.S. Appl. No. 17/070,323 mailed Oct. 4, 2023.
Corrected Notice of Allowance for U.S. Appl. No. 17/077,769 mailed Nov. 15, 2023.
Corrected Notice of Allowance for U.S. Appl. No. 17/077,769 mailed Nov. 6, 2023.
Corrected Notice of Allowance for U.S. Appl. No. 17/077,769 mailed Oct. 4, 2023.
Corrected Notice of Allowance for U.S. Appl. No. 17/180,041 mailed Oct. 4, 2023.
Examination Report for Australian Application No. 2019206421 mailed Sep. 29, 2023.
Extended Search Report for European Application No. 23189145.8 mailed Nov. 27, 2023.
Final Office Action for U.S. Appl. No. 17/078,472 mailed Oct. 23, 2023.
Issue Notification for U.S. Appl. No. 16/275,559 mailed Nov. 22, 2023.
Issue Notification for U.S. Appl. No. 17/070,323 mailed Oct. 18, 2023.
Issue Notification for U.S. Appl. No. 17/077,769 mailed Nov. 29, 2023.
Issue Notification for U.S. Appl. No. 17/180,041 mailed Oct. 18, 2023.
Non-Final Office Action for U.S. Appl. No. 16/952,327 mailed Oct. 13, 2023.
Non-Final Office Action for U.S. Appl. No. 17/069,570 mailed Oct. 2, 2023.
Non-Final Office Action for U.S. Appl. No. 17/070,670 mailed Oct. 30, 2023.
Non-Final Office Action for U.S. Appl. No. 17/176,344 mailed Oct. 31, 2023.
Notice of Allowance for U.S. Appl. No. 16/275,559 mailed Oct. 4, 2023.
Notice of Allowance for U.S. Appl. No. 17/077,769 mailed Sep. 27, 2023.
Notice of Allowance for U.S. Appl. No. 17/078,439 mailed Dec. 5, 2023.
Notice of Allowance for U.S. Appl. No. 17/173,944 mailed Nov. 8, 2023.
Notice of Allowance for U.S. Appl. No. 17/177,296 mailed Nov. 17, 2023.
Office Action for Japanese Application No. 2021-533242 mailed Nov. 8, 2023.
U.S. Appl. No. 18/511,532, filed Nov. 16, 2023.
Corrected Notice of Allowance for U.S. Appl. No. 16/952,389 mailed Feb. 20, 2024.
Corrected Notice of Allowance for U.S. Appl. No. 16/952,389 mailed Mar. 4, 2024.
Corrected Notice of Allowance for U.S. Appl. No. 16/952,444 mailed Mar. 13, 2024.
Corrected Notice of Allowance for U.S. Appl. No. 17/069,570 mailed Apr. 10, 2024.
Examination Report for European Application No. 21158196.2 mailed May 28, 2024.
Examination Report for European Application No. 21718229.4 mailed Mar. 17, 2022.
Final Office Action for U.S. Appl. No. 17/176,344 mailed Apr. 12, 2024.
Final Office Action for U.S. Appl. No. 17/528,807 mailed Apr. 24, 2024.
International Search Report and Written Opinion from International Application No. PCT/IB2023/059136 mailed Jan. 2, 2024.
International Search Report and Written Opinion from International Application No. PCT/IB2023/059137 mailed Mar. 21, 2024.
International Search Report and Written Opinion from International Application No. PCT/IB2023/059138 mailed Feb. 7, 2024.
International Search Report and Written Opinion from International Application No. PCT/IB2023/059141 mailed Mar. 22, 2024.
International Search Report and Written Opinion from International Application No. PCT/IB2023/059142 mailed Apr. 16, 2024.
International Search Report and Written Opinion from International Application No. PCT/IB2023/059143 mailed Mar. 14, 2024.
Invitation to Pay Additional Fees for International Application No. PCT/IB2023/059134 mailed Dec. 21, 2023.
Invitation to Pay Additional Fees for International Application No. PCT/IB2023/059137 mailed Jan. 2, 2024.

(56) References Cited

OTHER PUBLICATIONS

Invitation to Pay Additional Fees for International Application No. PCT/IB2023/059138 mailed Dec. 8, 2023.
Invitation to Pay Additional Fees for International Application No. PCT/IB2023/059141 mailed Dec. 22, 2023.
Invitation to Pay Additional Fees for International Application No. PCT/IB2023/059142 mailed Jan. 2, 2024.
Issue Notification for U.S. Appl. No. 16/952,389 mailed Mar. 13, 2024.
Issue Notification for U.S. Appl. No. 16/952,444 mailed Mar. 20, 2024.
Issue Notification for U.S. Appl. No. 17/078,439 mailed Apr. 3, 2024.
Issue Notification for U.S. Appl. No. 17/177,296 mailed Mar. 13, 2024.
Non-Final Office Action for U.S. Appl. No. 17/078,472 mailed Feb. 14, 2024.
Notice of Allowance for U.S. Appl. No. 16/952,327 mailed Apr. 29, 2024.
Notice of Allowance for U.S. Appl. No. 16/952,389 mailed Feb. 7, 2024.
Notice of Allowance for U.S. Appl. No. 16/952,444 mailed Feb. 15, 2024.
Notice of Allowance for U.S. Appl. No. 17/069,570 mailed Mar. 13, 2024.
Notice of Allowance for U.S. Appl. No. 17/078,439 mailed Feb. 27, 2024.
Notice of Allowance for U.S. Appl. No. 17/173,944 mailed Mar. 6, 2024.
Notice of Allowance for U.S. Appl. No. 17/177,296 mailed Feb. 14, 2024.
Notice of Missing Requirements for U.S. Appl. No. 18/447,025 mailed Feb. 1, 2024.
U.S. Appl. No. 18/444,972, filed Feb. 19, 2024.
U.S. Appl. No. 18/632,533, filed Apr. 11, 2024.
U.S. Appl. No. 18/632,545, filed Apr. 11, 2024.
U.S. Appl. No. 18/632,557, filed Apr. 11, 2024.
U.S. Appl. No. 18/632,569, filed Apr. 11, 2024.
U.S. Appl. No. 18/635,275, filed Apr. 15, 2024.
U.S. Appl. No. 18/635,286, filed Apr. 15, 2024.
U.S. Appl. No. 18/635,292, filed Apr. 15, 2024.
U.S. Appl. No. 18/637,653, filed Apr. 17, 2024.
U.S. Appl. No. 18/637,655, filed Apr. 17, 2024.
U.S. Appl. No. 18/637,667, filed Apr. 17, 2024.
U.S. Appl. No. 18/639,079, filed Apr. 18, 2024.
U.S. Appl. No. 18/639,087, filed Apr. 18, 2024.
U.S. Appl. No. 18/639,094, filed Apr. 18, 2024.
U.S. Appl. No. 18/639,098, filed Apr. 18, 2024.
U.S. Appl. No. 18/640,222, filed Apr. 19, 2024.
U.S. Appl. No. 18/640,260, filed Apr. 19, 2024.
U.S. Appl. No. 18/640,285, filed Apr. 19, 2024.
U.S. Appl. No. 18/640,303, filed Apr. 19, 2024.
U.S. Appl. No. 18/652,930, filed May 2, 2024.
U.S. Appl. No. 18/652,956, filed May 2, 2024.
U.S. Appl. No. 18/652,959, filed May 2, 2024.
U.S. Appl. No. 18/652,962, filed May 2, 2024.
U.S. Appl. No. 18/654,336, filed May 3, 2024.
U.S. Appl. No. 63/406,427, filed Sep. 14, 2022.
U.S. Appl. No. 63/432,496, filed Dec. 14, 2022.
U.S. Appl. No. 63/443,519, filed Feb. 6, 2023.
U.S. Appl. No. 63/470,259, filed Jun. 1, 2023.
Chang, et al., "Leveraging Device-Arterial Coupling to Determine Cardiac and Vascular State", IEEE Transactions on Biomedical Engineering, vol. 66, No. 10, Oct. 2019, pp. 2800-2808.
Keller, et al., "Dynamic Modulation of Device-Arterial Coupling to Determine Cardiac Output and Vascular Resistance", Annals of Biomedical Engineering, vol. 48, No. 9, Sep. 2020, pp. 2333-2342.

\* cited by examiner

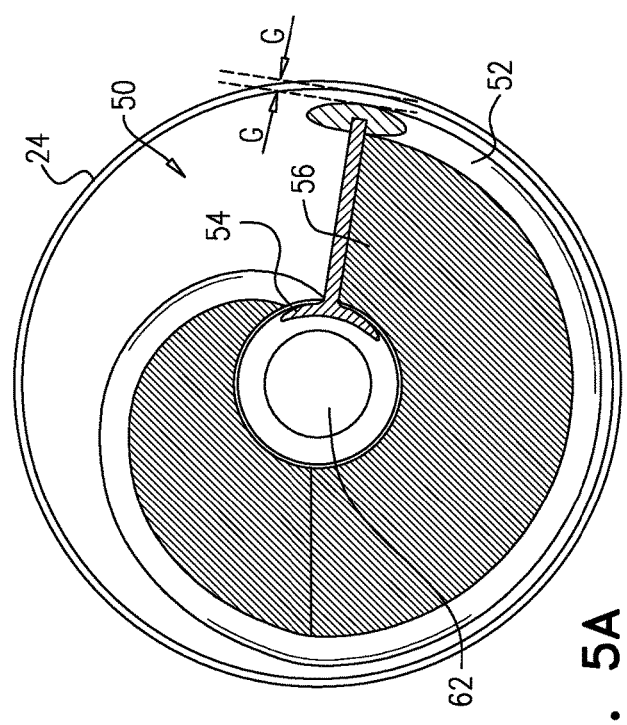
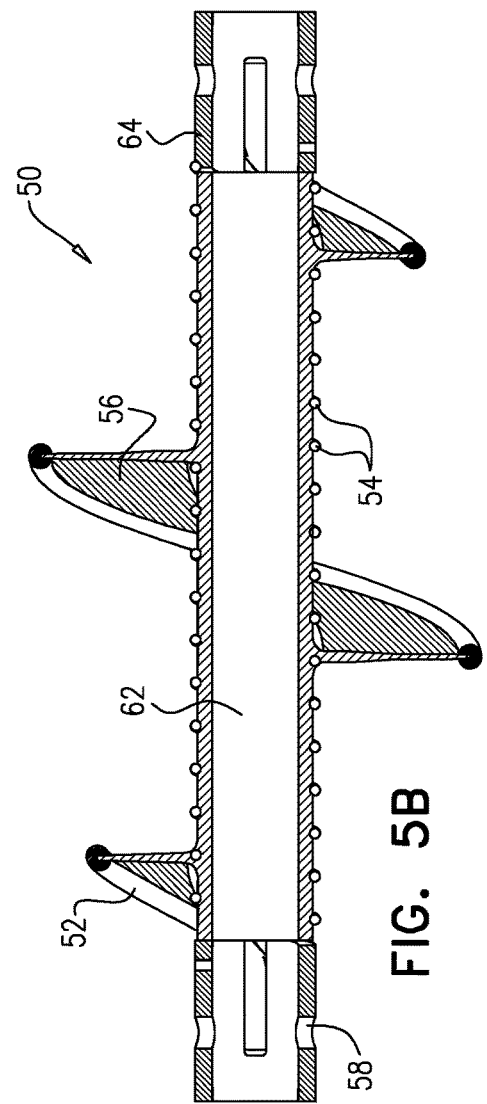
FIG. 5A
FIG. 5B

VENTRICULAR ASSIST DEVICE

CROSS-REFERENCES TO RELATED APPLICATIONS

The present application is a continuation of U.S. application Ser. No. 16/277,411 to Tuval (published as US 2019/0175806), entitled "Ventricular assist device," filed Feb. 15, 2019, which is a continuation of International Application No. PCT/IL2017/051158 to Tuval (published as WO 18/078615), entitled "Ventricular assist device," filed Oct. 23, 2017, which claims priority from:

U.S. Provisional Patent Application No. 62/412,631 to Tuval, entitled "Ventricular assist device," filed Oct. 25, 2016; and U.S. Provisional Patent Application No. 62/543,540 to Tuval, entitled "Ventricular assist device," filed Aug. 10, 2017.

U.S. Provisional Patent Application No. 62/412,631 and U.S. Provisional Patent Application 62/543,540 are incorporated herein by reference.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are used to assist cardiac circulation, for patients suffering from a failing heart. Most commonly a left-ventricular assist device is applied to a defective heart, in order to assist left-ventricular functioning. In some cases, a right-ventricular assist device is used, in order to assist right-ventricular functioning.

SUMMARY OF EMBODIMENTS

In accordance with some applications of the present invention, an impeller includes a helical elongate element, a spring that is disposed inside of, and coaxially with, the helical elongate element, and a film of material supported between the helical elongate element and the spring. For some applications, the impeller comprises a portion of a ventricular assist device configured to assist ventricular functioning of a subject, e.g., a left-ventricular assist device is configured to assist left ventricular functioning of a subject. The ventricular assist device typically includes an elongate tube configured to traverse the subject's aortic valve, such that a proximal end of the tube is disposed within the subject's aorta and a distal end of the tube is disposed within the subject's left ventricle. The elongate tube includes a frame formed from a self-expandable shape-memory alloy, and a blood impermeable material that is disposed upon the frame. The ventricular assist device includes a pump, which typically includes the impeller and a cage disposed around the impeller. The impeller is typically configured to pump blood out of the subject's left ventricle and into the subject's aorta, by rotating. Typically, the impeller also impedes backflow of blood across the aortic valve, from the aorta into the left ventricle.

For some applications, the cage is integrally formed with the elongate tube such that the cage is disposed within the frame of the elongate tube at the proximal end of the elongate tube. The pump is thereby disposed within a proximal portion of the elongate tube, and a longitudinal axis of the pump is thereby aligned with a longitudinal axis of the elongate tube. Alternatively, the cage is not integrally formed with the elongate tube.

There is therefore provided, in accordance with some applications of the present invention, apparatus including:

an impeller including:
  at least one helical elongate element;
  a spring, the spring being disposed inside of, and coaxially with, the helical elongate element; and
  a film of material supported between the helical elongate element and the spring.

In some applications, the impeller includes a plurality of helical elongate elements, and the film of material is supported between the plurality of helical elongate elements and the spring, such that the impeller defines a plurality of blades.

In some applications, when the impeller is disposed in a non-radially-constrained configuration, a pitch of the helical elongate element varies along a length of the helical elongate element.

In some applications, when the impeller is disposed in a non-radially-constrained configuration, a pitch of the helical elongate element is greater than 1 mm.

In some applications, when the impeller is disposed in a non-radially-constrained configuration, a pitch of the helical elongate element is less than 20 mm.

In some applications, the impeller is configured to be placed inside a blood vessel of a subject and to pump blood through the subject's blood vessel by the impeller rotating.

In some applications, the impeller is configured to be placed in an aorta of a subject and to pump blood from a left ventricle of the subject, by the impeller rotating.

In some applications, the impeller is configured to be placed in a ventricle of a subject and to pump blood from the ventricle, by the impeller rotating.

In some applications, the impeller is configured to be placed in an aorta of a subject and to impede backflow of blood from the aorta into a left ventricle of the subject.

In some applications, the impeller is configured to be radially constrained by the helical elongate element and the spring being axially elongated, and in response to the axial elongation of the helical elongate element and the spring, the film is configured to change shape without the film of material breaking.

In some applications, the apparatus further includes:
  an elongate tube configured to traverse an aortic valve of a subject, such that a proximal end of the tube is disposed within an aorta of the subject and a distal end of the tube is disposed within a left ventricle of the subject, the elongate tube including:
    a frame formed from a shape-memory alloy; and
    a blood impermeable material that is disposed upon the frame; and
  a cage disposed around the impeller,
  the elongate tube being configured to be disposed around the cage and the impeller, and the impeller being configured to pump blood from the left ventricle to the aorta, by rotating.

In some applications, the spring, when disposed in a non-radially-constrained configuration thereof, is configured by virtue of its rigidity, to stabilize the impeller with respect to the elongate tube, during rotation of the impeller, such that a gap between an outer edge of the impeller and an inner surface of the elongate tube is maintained.

In some applications:
the spring defines a lumen therethrough, and
the impeller further includes:
   proximal and distal bushings; and
   a rigid shaft configured to extend from the proximal bushing to the distal bushing via the lumen defined by the spring, the rigid shaft being configured to stabilize the impeller with respect to the elongate tube, during rotation of the impeller, such that a gap between an outer edge of the impeller and an inner surface of the elongate tube is maintained.

In some applications, the cage is integrally formed with the frame of the elongate tube such that the cage is disposed within the frame of the elongate tube at the proximal end of the elongate tube, the impeller thereby being disposed within a proximal portion of the elongate tube, and a longitudinal axis of the impeller thereby being aligned with a longitudinal axis of the elongate tube.

In some applications, a gap between an outer edge of the impeller and an inner surface of the elongate tube is less than 1 mm.

In some applications, the gap between the outer edge of the impeller and the inner surface of the elongate tube is less than 0.4 mm.

In some applications, the impeller is configured to be stabilized with respect to the elongate tube, such that, during rotation of the impeller, the gap between the impeller and the elongate tube is maintained.

In some applications, the cage is not integrally formed with the frame of the elongate tube.

In some applications, the apparatus further includes one or more support arms that are configured to extend from the cage to the frame of the elongate tube, and that are configured, during rotation of the impeller, to stabilize a distal end of the impeller with respect to the frame of the elongate tube, such that a gap between an outer edge of the impeller and an inner surface of the elongate tube is maintained.

In some applications, the support arms are configured to be slidable with respect to the frame of the elongate tube.

In some applications, the support arms are configured to be coupled to the frame of the elongate tube.

In some applications, the apparatus further includes a plurality of winged projections that are coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

In some applications, the elongate tube is configured to be inserted into a body of the subject transcatheterally, while in a radially-constrained configuration, and the winged projections are configured to become folded, when the elongate tube is in its radially-constrained configuration.

In some applications, the spring defines a lumen therethrough, and the impeller further includes:
   proximal and distal bushings; and
   a rigid shaft configured to extend from the proximal bushing to the distal bushing via the lumen defined by the spring.

In some applications, the rigid shaft is configured to maintain the proximal bushing and the distal bushing aligned with each other.

In some applications, the impeller is configured to be placed into a body of a subject, and subsequent to placement of the spring inside the subject's body, the rigid shaft is configured to be placed within the lumen defined by the spring.

In some applications, the impeller is configured to be placed into a body of a subject, and the rigid shaft is configured to be disposed within the lumen defined by the spring, during placement of the impeller into the subject's body.

In some applications, the impeller further includes proximal and distal bushings, and the spring, when disposed in a non-radially-constrained configuration thereof, is configured, by virtue of its rigidity, to maintain the proximal bushing and the distal bushing aligned with each other.

In some applications, the spring, when disposed in the non-radially-constrained configuration thereof, is configured such that there are substantially no gaps between windings of the spring and adjacent windings thereto.

There is further provided, in accordance with some applications of the present invention, a method including:
   placing within a blood vessel of a subject an impeller, the impeller including:
      at least one helical elongate element;
      a spring, the spring being disposed inside of, and coaxially with, the helical elongate element; and
      a film of material supported between the helical elongate element and the spring;
   pumping blood through the subject's blood vessel, using the impeller.

The present invention will be more fully understood from the following detailed description of embodiments thereof, taken together with the drawings, in which:

BRIEF DESCRIPTION OF THE DRAWINGS

FIGS. 5A and 5B are schematic illustrations of respective cross-sectional views of an impeller of the ventricular assist device shown in FIGS. 4A and 4B in accordance with some applications of the present invention;

DETAILED DESCRIPTION OF EMBODIMENTS

Figure 1B:
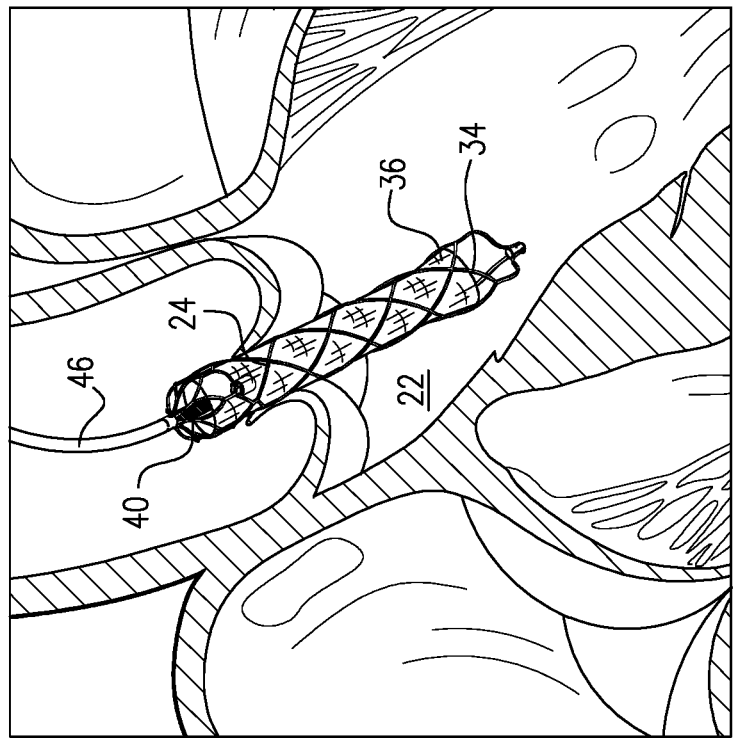
FIGS. 1A and 1B are schematic illustrations of a ventricular assist device disposed in a subject's left ventricle, in accordance with some applications of the present invention.
Figure 1A:
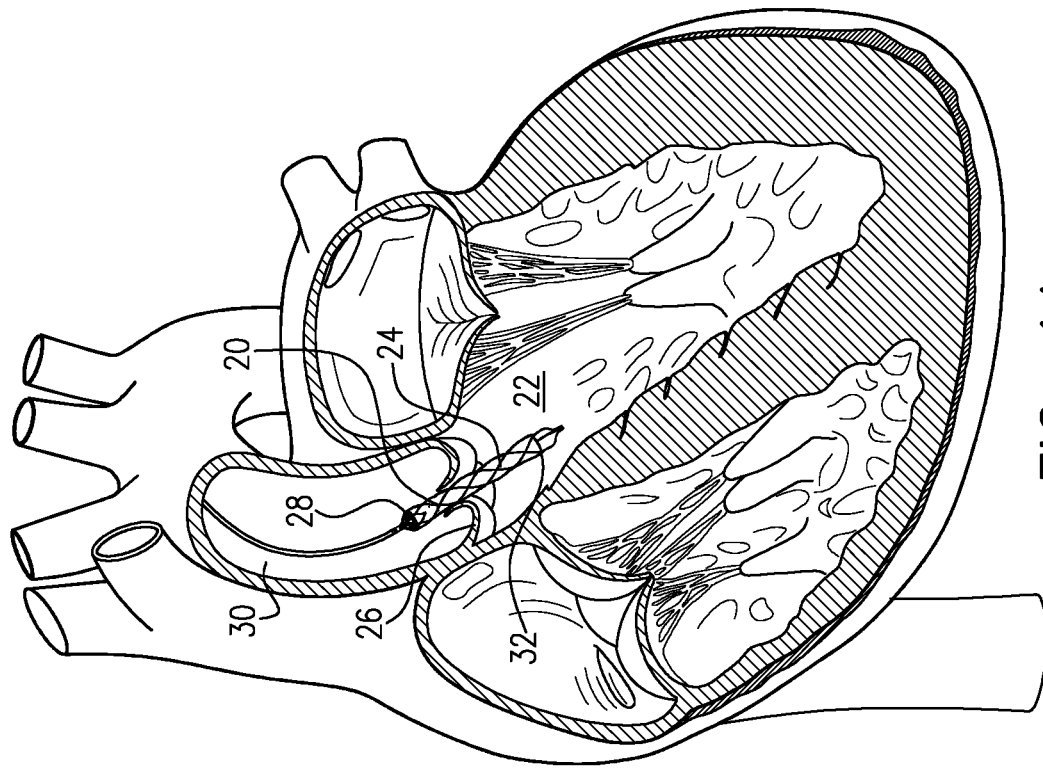

Reference is now made to FIGS. 1A and 1B, which are schematic illustrations of a ventricular assist device 20 disposed in a subject's left ventricle 22, in accordance with some applications of the present invention. The ventricular assist device includes an elongate tube 24, which traverses an aortic valve 26 of the subject, such that a proximal end 28 of the elongate tube is disposed in an aorta 30 of the subject and a distal end 32 of the tube is disposed within left ventricle 22. The elongate tube typically includes a radially-expandable frame 34 formed from a self-expandable shape-memory alloy, such as nitinol, and a blood impermeable material 36 that is disposed upon the frame. For example, the blood impermeable material may include polyurethane, polyester, and/or silicone. Typically, the frame provides the elongate tube with rigidity, and the blood impermeable material provides the elongate tube with blood impermeability. Further typically, the shape memory alloy of the frame is shape set such the frame assumes its tubular shape in the absence of any forces being applied to the tube. Typically, device 20 is inserted into the left ventricle transcatheterally (e.g., via the brachial artery), while the tube is in a radially constrained state. Upon being released from the catheter, the tube automatically assumes it tubular shape, due to the frame expanding. A pump 40 is disposed within the elongate tube (e.g., within a proximal portion of the elongate tube, as shown), and is configured to pump blood through the elongate tube from the left ventricle into the aorta, to thereby assist left ventricular functioning.

Figure 2:
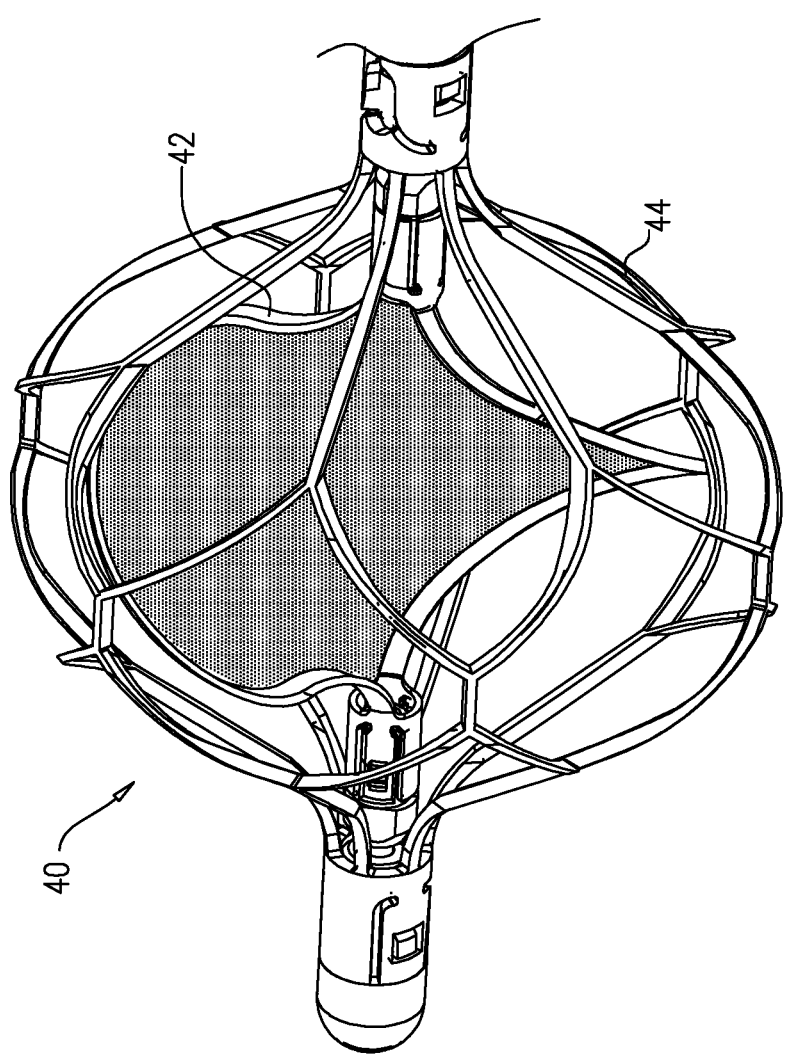
FIG. 2 is a schematic illustration of a pump that includes an impeller and a cage, in accordance with some applications of the present invention.

FIG. 2 is a schematic illustration of pump 40, in accordance with some applications of the present invention. Pump 40 typically includes a radially-expandable impeller 42 disposed inside a radially-expandable cage 44. Typically, pump 40 is inserted into the left ventricle transcatheterally, while the impeller and the cage are in radially constrained configurations. The impeller and the cage typically include a shape memory alloy (such as nitinol), which is shape set such that the impeller and the cage assume non-radially-constrained (i.e., radially-expanded) configurations thereof in the absence of any radially-constraining force acting upon the impeller and the cage. Thus, typically, the cage and the impeller radially expand upon being released from the distal end of the catheter via which they are inserted. For some applications, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference. In general, pump 40 is generally similar to the blood pumps described in WO 14/141284 to Schwammenthal, WO 15/177793 to Schwammenthal, and/or WO 16/185473 to Schwammenthal, all of which are incorporated herein by reference. Typically, pump 40 pumps blood through the elongate tube from the left ventricle into the aorta, by the impeller rotating. For some applications, a rotating cable 46 (FIG. 1B) rotates the impeller. Typically, the rotating cable is rotated by a motor (not shown) which is disposed outside the subject's body, or inside the subject's body.

For some applications, pump 40 is disposed at a proximal end of the elongate tube, such that the pump is disposed within the aorta. For some applications, the pump is disposed at the distal end of the elongate tube, such that the pump is disposed within the subject's ventricle.

Figure 3:
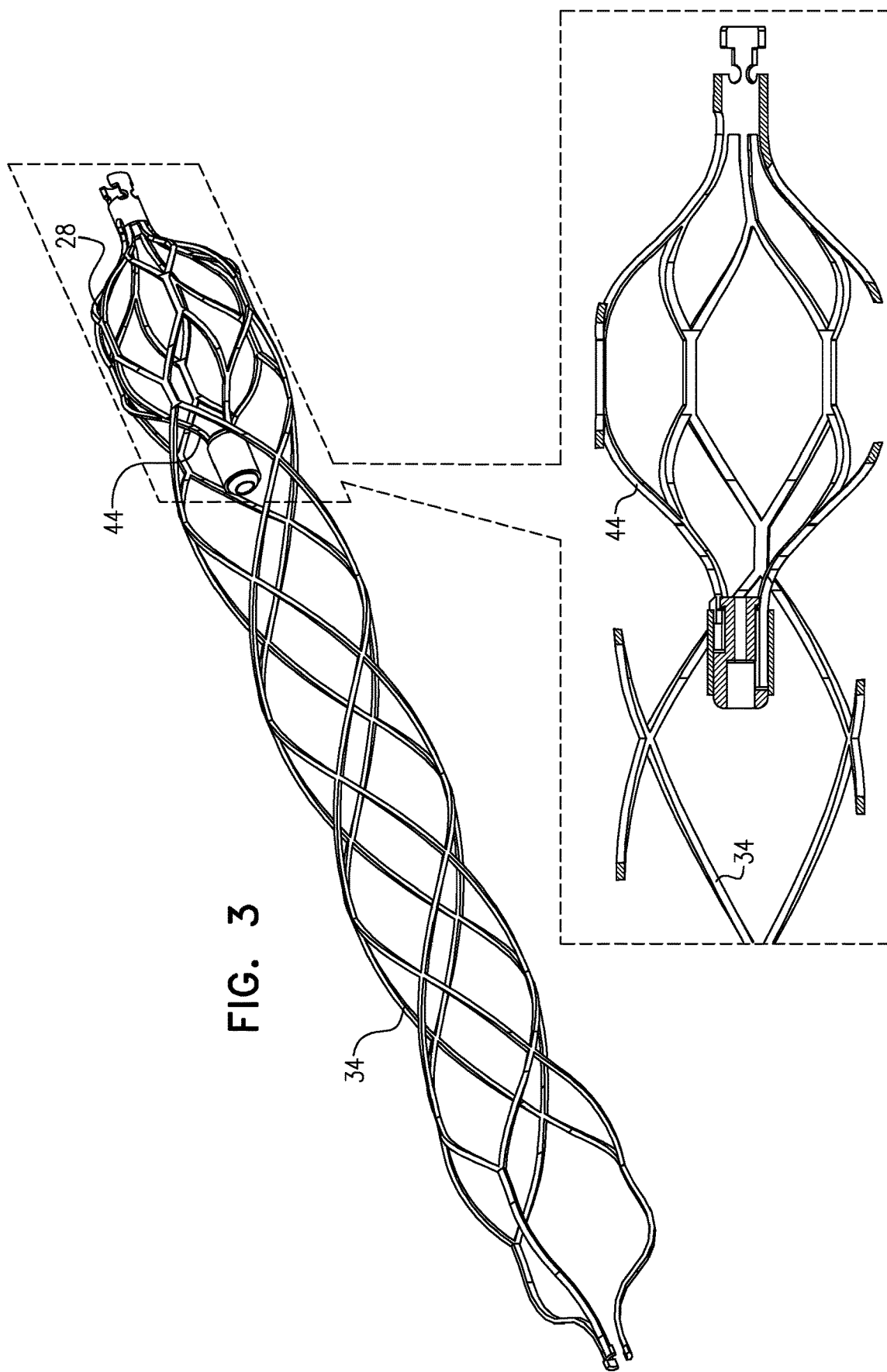
FIG. 3 is a schematic illustration of a frame of an elongate tube of the ventricular assist device, and a cage of the impeller of the ventricular assist device, in accordance with some applications of the present invention.

Reference is now made to FIG. 3, which is a schematic illustration of frame 34 of elongate tube 24 and cage 44 of pump 40 of ventricular assist device 20, in accordance with some applications of the present invention. As shown, for some applications, the cage is integrally formed with the frame of the elongate tube, such that the cage is disposed within the frame of the elongate tube at the proximal end of the elongate tube. Typically, by virtue of the cage being disposed within the frame of the elongate tube at the proximal end of the elongate tube, pump 40 is disposed within a proximal portion of the elongate tube, and the longitudinal axis of the pump is aligned with the longitudinal axis of the elongate tube. For some applications, frame 34 of elongate tube 24 and cage 44 are cut from a single piece (e.g., a single tube) of a shape memory material (e.g., a shape-memory alloy, such as nitinol). Typically, by virtue of being cut from the single piece of the shape-memory the region of the tube in which the cage is disposed is able to be radially compressed to a smaller diameter than would be possible if the cage were cut from a separate piece of the shape memory material and inserted inside the elongate tube or vice versa, ceteris paribus.

Figure 4A:
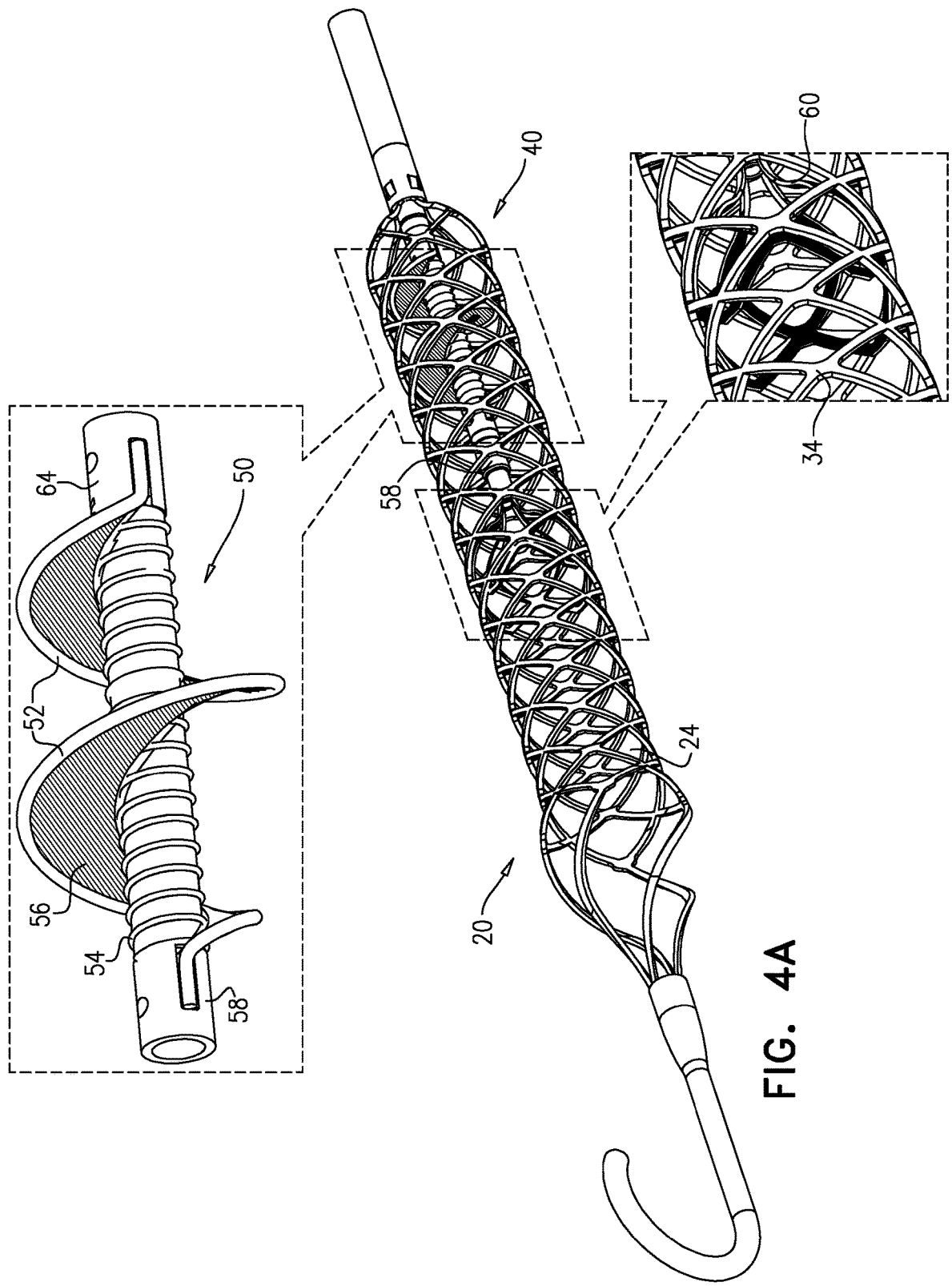
FIGS. 4A and 4B are schematic illustrations of a ventricular assist device, in accordance with some additional applications of the present invention.

Reference is now made to FIG. 4A, which is a schematic illustration of a ventricular assist device 20, in accordance with some additional applications of the present invention. For some applications, pump 40 is generally as shown in FIG. 4A. Typically, the pump includes an impeller 50, which includes an outer helical elongate element 52, which winds around a central axial spring 54, such that the helix defined by the helical elongate element is coaxial with the central axial spring. For some applications, the helical elongate element and the central axial spring are made of a shape memory material, e.g., a shape memory alloy such as nitinol. Typically, the helical elongate element and the central axial spring support a film 56 of a material (e.g., a polymer, such as polyurethane, and/or silicone) therebetween. The helical elongate element, the axial spring and the film define the impeller blade, with the helical elongate element defining the outer edge of the impeller blade (and thereby defining the outer edge of the impeller), and the axial spring defining the axis of the impeller blade. For some applications, sutures (e.g., polyester sutures, not shown) are wound around the helical elongate element, e.g., as described in WO 14/141284, which is incorporated herein by reference. Typically, the sutures are configured to facilitate bonding between the film of material (which is typically a polymer, such as polyurethane, or silicone) and the helical elongate element (which is typically a shape memory alloy, such as nitinol). For some applications, sutures (e.g., polyester sutures, not shown) are wound around spring 54. Typically, the sutures are configured to facilitate bonding between the film of material (which is typically a polymer, such as polyurethane, or silicone) and the spring (which is typically a shape memory alloy, such as nitinol).

Typically, proximal ends of both spring 54 and helical elongate element 52 are coupled to a proximal bushing (i.e., sleeve bearing) 64 of the impeller, such that the proximal ends of both spring 54 and helical elongate element 52 are disposed at a similar radial distance from the longitudinal axis of the impeller, as each other. Similarly, typically, distal ends of both spring 54 and helical elongate element 52 are coupled to a distal bushing 58 of the impeller, such that the distal ends of both spring 54 and helical elongate element 52 are disposed at a similar radial distance from the longitudinal axis of the impeller, as each other.

For some such applications, frame 34 of elongate tube 24 does not include a cage integrally formed therewith, as described hereinabove with reference to FIG. 3. Rather, for some such applications, a distal bushing 58 of the impeller is stabilized with respect to the elongate tube, by means of one or more support arms 60 that extend radially outwardly from the distal bushing of the impeller to frame 34 of elongate tube 24. As shown in FIG. 4A, for some applications, the support arms are not coupled to frame 34 of the elongate tube, but are configured to engage an inner surface of the elongate tube, to thereby stabilize the distal bushing of the impeller with respect to the elongate tube. For such applications, the support arms are typically configured to be moveable with respect to the elongate tube, by the support arms sliding along the inner surface of the elongate tube. Alternatively, even if the support arms are not integrally formed with frame 34 of the elongate tube, the support arms are coupled to frame 34 of the elongate tube (e.g., via welding, suturing, and/or an adhesive), such that, at least at the locations at which the support arms are coupled to the frame of the elongate tube, the support arms cannot undergo motion relative to the elongate tube. Further alternatively, the device includes support arms that are integrally formed with frame 34 of the elongate tube, as shown in FIG. 4B.

Figure 4B:
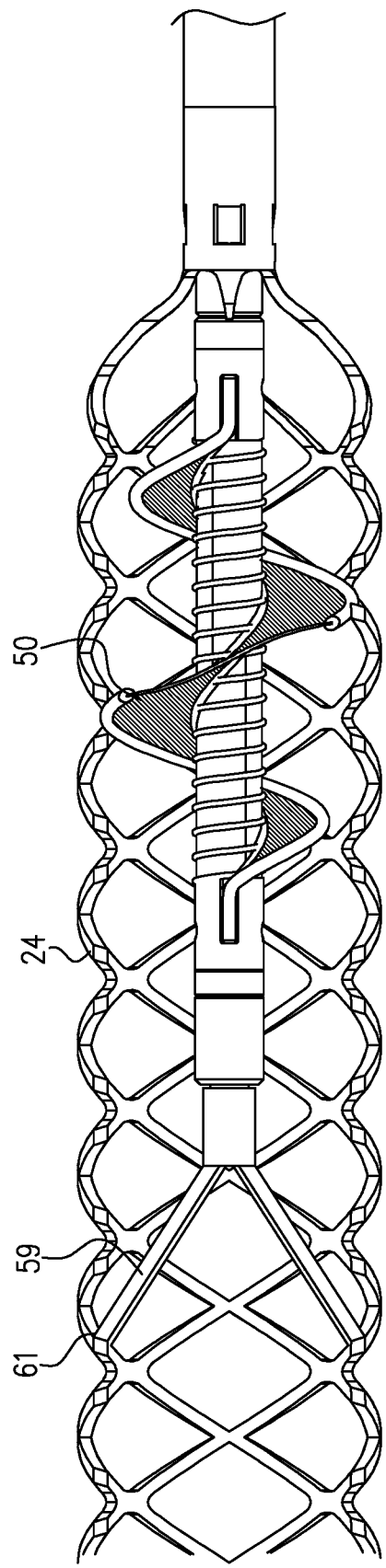

Reference is now made to FIG. 4B, which is a schematic illustration of device 20, the device including support arms 59, which are integrally formed with frame 34 of the elongate tube 24, the support arms being coupled to frame 34 at coupling points 61, in accordance with some applications of the present invention. Typically, the support arms are configured to extend from the distal bushing of the impeller to the coupling points, and are configured to thereby stabilize the distal bushing of the impeller with respect to the elongate tube.

With respect to device 20 as shown in FIGS. 4A-B, it is noted that for some applications, impeller 50 is disposed at a proximal end of the elongate tube, as shown, such that, during use of device 20, the impeller is disposed within the aorta, and pumps blood from the left ventricle into the aorta by rotating within the aorta. For some applications (not shown), the impeller is disposed at the distal end of the elongate tube, such that, during use of device 20, the impeller is disposed within the ventricle, and pumps blood out of the ventricle, by rotating within the ventricle. In general, in the context of the present application, the term "blood vessel" should be interpreted as including a ventricle. Similarly, an impeller that is described as being placed within a blood vessel, should be interpreted as including an impeller that is placed within a ventricle.

Figure 5C:
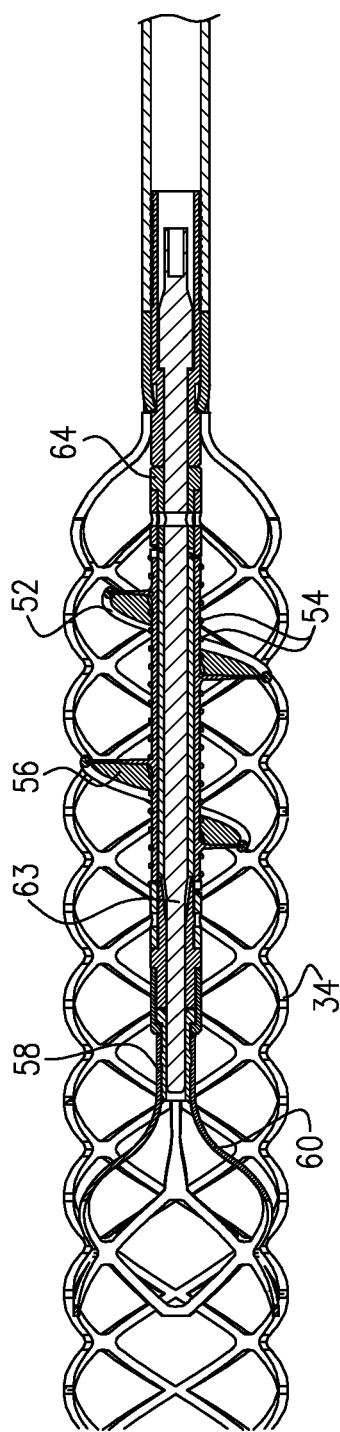
FIG. 5C is a schematic illustration of a cross-sectional view of the ventricular assist device shown in FIGS. 4A and 4B, in accordance with some applications of the present invention.

Reference is now made to FIGS. 5A and 5B, which are schematic illustrations of cross-sectional views of impeller 50, respectively perpendicularly to the longitudinal axis of the impeller, and along the longitudinal axis of the impeller, in accordance with some applications of the present invention. Reference is also made to FIG. 5C, which is a schematic illustration of a cross-sectional view of ventricular assist device 20 along the longitudinal axis of the device, in accordance with some applications of the present invention. As shown in FIG. 5B for example, spring 54 defines a lumen 62 therethrough. For some applications, a rigid shaft 63 is disposed along the lumen at least from proximal bushing 64 of the impeller to distal bushing 58. The rigid shaft is configured to impart rotational motion from the proximal bushing to the distal bushing, and/or to maintain the distal bushing and the proximal bushing aligned with each other and aligned with the longitudinal axis of the elongate tube. Alternatively or additionally, spring 54 itself acts as a shaft. Thus, for some applications, the spring imparts rotational motion from the proximal bushing to the distal bushing, and/or maintains the distal bushing and the proximal bushing aligned with each other and aligned with the longitudinal axis of the elongate tube. For some such applications, the spring is configured such that, when the spring is disposed in a non-radially-constrained configuration, there are substantially no gaps between windings of the spring and adjacent windings thereto.

Figure 5D:
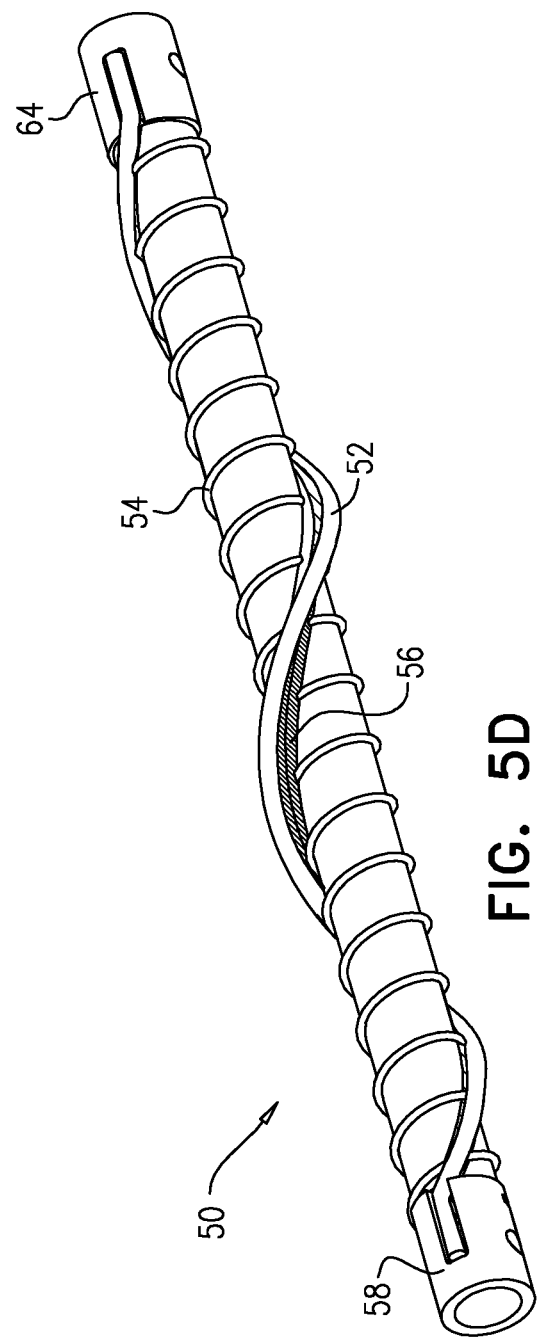
FIG. 5D is a schematic illustration of the impeller of the ventricular assist device shown in FIGS. 4A and 4B in a radially-constrained configuration, in accordance with some applications of the present invention.

Reference is now made to FIG. 5D, which is a schematic illustration of impeller 50 in a radially constrained (i.e., axially-elongated) configuration, in accordance with some applications of the present invention. Typically, pump 40 is inserted into the left ventricle transcatheterally, while impeller 50 is in its radially constrained configuration. As shown, in the radially constrained configuration, both helical elongate element 52 and central axial spring 54 become axially elongated, and radially constrained. Typically film 56 of the material (e.g., silicone) changes shape to conform to the shape changes of the helical elongate element and the axial support spring, both of which support the film of material. Typically, using a spring to support the inner edge of the film allows the film to change shape without the film becoming broken or collapsing inwardly onto a shaft disposed within lumen 62, due to the spring providing a large surface area to which the inner edge of the film bonds. For some applications, using a spring to support the inner edge of the film reduces a diameter to which the impeller can be radially constrained, relative to if, for example, a rigid shaft was to be used to support the inner edge of the film, since the diameter of the spring itself can be reduced by axially elongating the spring. As described hereinabove and as shown in FIG. 5C, for some applications, rigid shaft 63 is disposed along lumen 62 (defined by spring 54) at least from proximal bushing 64 of the impeller to distal bushing 58. For some applications, the rigid shaft is disposed inside the lumen even during the transcatheteral insertion of the impeller into the subject's left ventricle. Alternatively, the rigid shaft is advanced into lumen 62 once the impeller has already been released from the insertion catheter, and is disposed inside with subject's ventricle.

Referring again to FIG. 5A, typically there is a gap G, between the outer edge of the impeller and the inner surface of elongate tube 24, even at a location at which the span of the impeller is at its maximum. For some applications, it is desirable that the gap between the outer edge of the blade of the impeller and elongate tube 24 be relatively small, in order for the impeller to efficiently pump blood from the subject's left ventricle into the subject's aorta. However, it is also desirable that a gap between the outer edge of the blade of the impeller and elongate tube 24 be maintained, for example, in order to reduce a risk of hemolysis. For some applications, the gap G between the outer edge of the impeller and the inner surface of elongate tube 24, at the location at which the span of the impeller is at its maximum, is greater than 0.05 mm (e.g., greater than 0.1 mm), and/or less than 1 mm (e.g., less than 0.4 mm), e.g., 0.05 mm-1 mm, or 0.1 mm-0.4 mm). As described hereinabove, for some applications, distal bushing 58 of the impeller is stabilized with respect to the elongate tube, by means of one or more support arms 60, or support arms 59. For some applications, by stabilizing distal bushing 58 of the impeller with respect to the elongate tube, even a relatively small gap between the outer edge of the blade of the impeller and elongate tube 24 (e.g., a gap that is as described above) is maintained, during rotation of the impeller. Alternatively or additionally, a rigid shaft is inserted along the axis of the impeller via lumen 62 defined by spring 54, and the rigid shaft stabilizes distal bushing 58 of the impeller with respect to the elongate tube, such that even a relatively small gap between the outer edge of the blade of the impeller and elongate tube 24 (e.g., a gap that is as described above) is maintained, during rotation of the impeller. Further alternatively or additionally, spring 54 is sufficiently rigid as to stabilize distal bushing 58 of the impeller with respect to the elongate tube, such that even a relatively small gap between the outer edge of the blade of the impeller and elongate tube 24 (e.g., a gap that is as described above) is maintained, during rotation of the impeller.

Typically, the pitch of helical elongate element 52, when impeller 50 is in a non-radially-constrained configuration (e.g., inside the subject's ventricle), is greater than 1 mm (e.g., greater than 6 mm), and/or less than 20 mm (e.g., less than 10 mm). Typically, ceteris paribus, the greater the pitch of the helical elongate element (and therefore the impeller blade), the greater the blood flow that is generated by the impeller. Therefore, as described, the pitch of the helical elongate element 52, when impeller 50 is in the non-radially-constrained configuration, is typically greater than 1 mm (e.g., greater than 6 mm). On the other hand, it is typically desirable that the impeller occludes backflow from the subject's aorta into the subject's left ventricle during diastole. Ceteris paribus, it is typically the case that the smaller the pitch of the helical elongate element (and therefore the impeller blade), the greater the occlusion that is provided by the impeller. Therefore, as described, the pitch of the helical elongate element 52, when impeller 50 is in the non-radially-constrained configuration, is typically less than 20 mm (e.g., less than 10 mm).

For some applications, the pitch of the helical elongate element (and therefore the impeller blade) varies along the length of the helical elongate element, at least when the impeller is in a non-radially-constrained configuration. Typically, for such applications, the pitch increases from the distal end of the impeller (i.e., the end that is inserted further into the subject's body, and that is placed upstream with respect to the direction of antegrade blood flow) to the proximal end of the impeller (i.e., the end that is placed downstream with respect to the direction of antegrade blood flow), such that the pitch increases in the direction of the blood flow. Typically, the blood flow velocity increases along the impeller, along the direction of blood flow. Therefore, the pitch is increased along the direction of the blood flow, such as to further accelerate the blood.

For some applications (not shown), impeller 50 is generally as shown in FIGS. 4A-5D, but the impeller includes a plurality of helical elongate elements. For example, the impeller may include two or three helical elongate elements. Typically, the film of material is supported between the plurality of helical elongate elements and the spring, such that the impeller defines a plurality of blades. Typically, the number of impeller blades corresponds to the number of helical elongate elements that are disposed upon the impeller, e.g., as is generally described in WO 14/141284 to Schwammenthal, which is incorporated herein by reference.

Figure 6A:
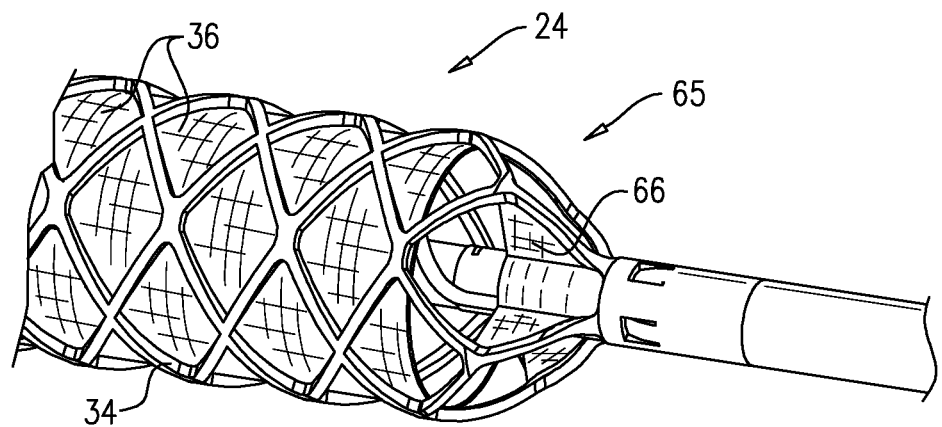
FIGS. 6A and 6B are schematic illustrations of a stator of a ventricular assist device, in accordance with some applications of the present invention.
Figure 6B:
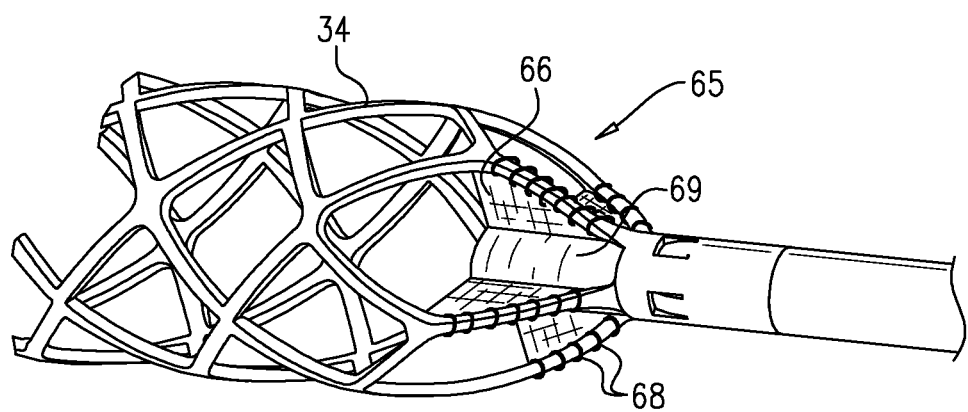

Reference is now made to FIGS. 6A and 6B, which are schematic illustrations of a stator 65 of ventricular assist device 20, in accordance with some applications of the present invention. FIG. 6B shows the stator in the absence of some other elements of the ventricular assist device, for illustrative purposes. For some applications, as shown, stator 65 is disposed within a proximal portion of frame 34 of elongate tube 24. Typically, the stator includes a plurality of (e.g., more than 2, and/or less than 8) winged projections 66 that, when device 20 is in a non-radially constrained configuration, extend from frame 34, and that are made of a flexible material, e.g., a polymer, such as polyurethane, and/or silicone. The winged projections are typically configured to define planes that are parallel to the longitudinal axis of the elongate tube, and are thereby configured to stabilize turbulent blood flow that is generated by the impeller, by directing blood flow along the direction of the longitudinal axis of the elongate tube.

It is noted that, as shown in FIG. 6A, typically elongate tube 24 includes blood impermeable material 36 that is disposed upon frame 34 of the tube. For example, the blood impermeable material may include polyurethane, polyester, or silicone, as described hereinabove. It is noted that, typically, the elongate tube includes the blood impermeable material, even though, for illustrative purposes, the blood impermeable material of the tube is not shown in all of the figures of the present application.

As shown in FIG. 6B, for some applications, sutures 68 are wound around portions of frame 34, in order to facilitate coupling between the winged projections and frame 34, in accordance with the techniques described hereinabove. For some applications, the winged projections extend from frame 34 to an axial support element 69. Typically, the axial support element is a tubular element formed of metal, plastic, and/or a polymer (such as polyurethane and/or silicone). For some applications, stator 65 is integrally formed with frame 34 of elongate tube 24. Alternatively or additionally, the stator is formed separately from the elongate tube.

As described hereinabove, typically, device 20 is inserted into the subject's ventricle transcatheterally, while elongate tube 24 is in a radially constrained state. Upon being released from the catheter, the tube automatically assumes it tubular shape, due to frame 34 of elongate tube 24 self-expanding. Typically, the stator is inserted into subject's left ventricle inside the elongate tube. During the insertion, the winged projections of the stator are in folded states, and do not substantially increase the minimal diameter to which the elongate tube can be radially-constrained, relative to if the tube did not contain the winged projections. Upon frame 34 of the elongate tube expanding, the winged projections are configured to automatically assume their winged configurations, due to the winged projections being coupled to frame 34.

It is noted that, although FIGS. 1A and 1B show ventricular assist device 20 in the subject's left ventricle, for some applications, device 20 is placed inside the subject's right ventricle, such that the device traverses the subject's pulmonary valve, and techniques described herein are applied, mutatis mutandis. Alternatively or additionally, device 20 and/or a portion thereof (e.g., impeller 50, even in the absence of elongate tube 24) is placed inside a different portion of the subject's body, in order to assist with the pumping of blood from that portion. For example, device 20 and/or a portion thereof (e.g., impeller 50, even in the absence of elongate tube 24) may be placed in a blood vessel and may be used to pump blood through the blood vessel. For some applications, device 20 and/or a portion thereof (e.g., impeller 50, even in the absence of elongate tube 24) is configured to be placed within the subclavian vein or jugular vein, at junctions of the vein with a lymph duct, and is used to increase flow of lymphatic fluid from the lymph duct into the vein, mutatis mutandis.

Figure 7A:
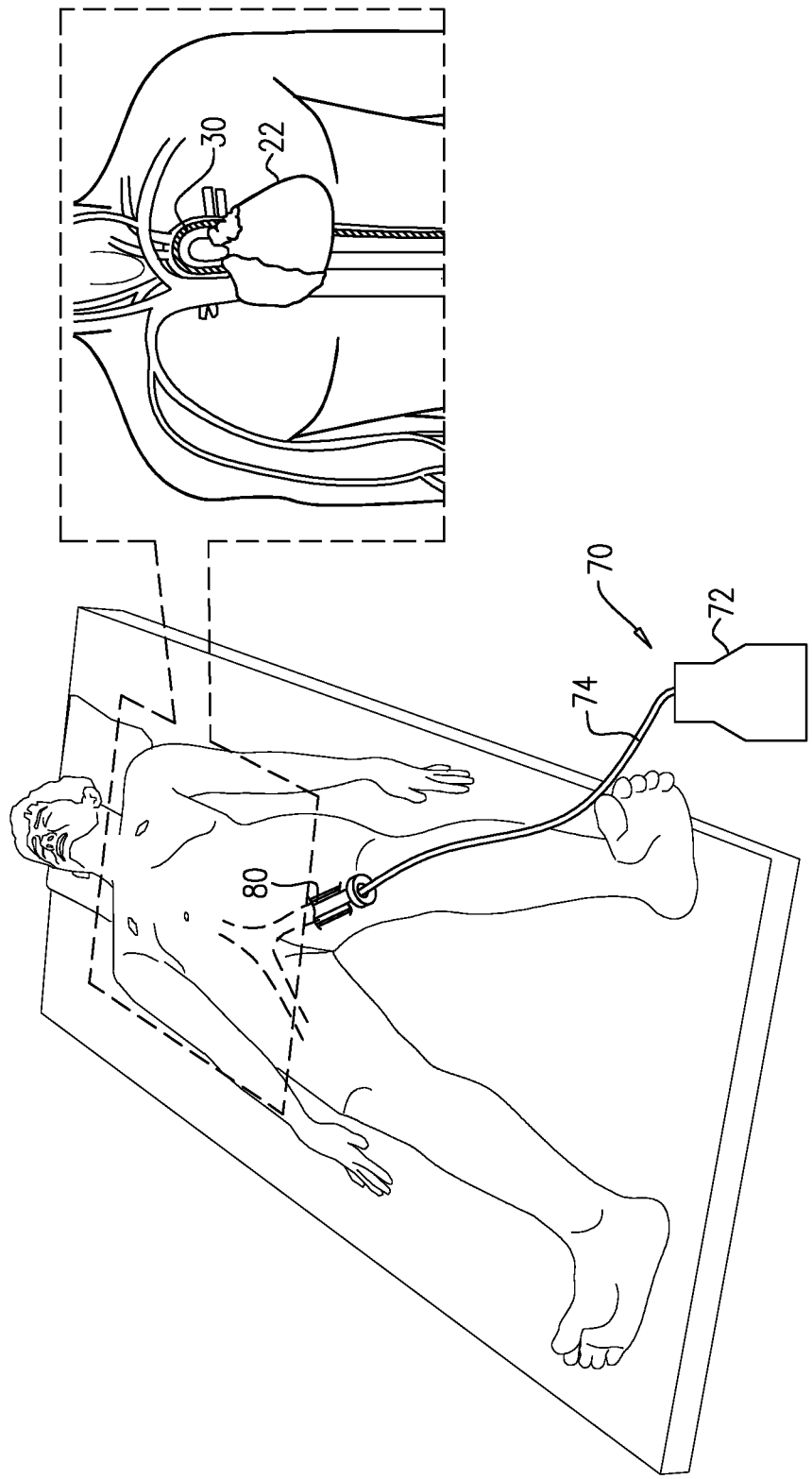
FIGS. 7A, 7B, and 7C are schematic illustrations of a ventricular assist device that includes a centrifugal pump, in accordance with some applications of the present invention.
Figure 7C:
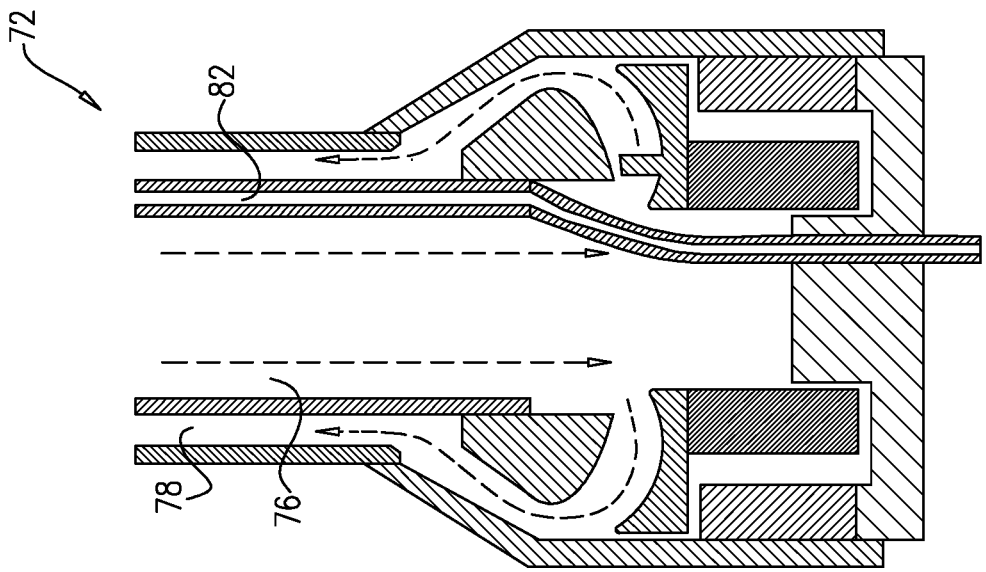
Figure 7B:
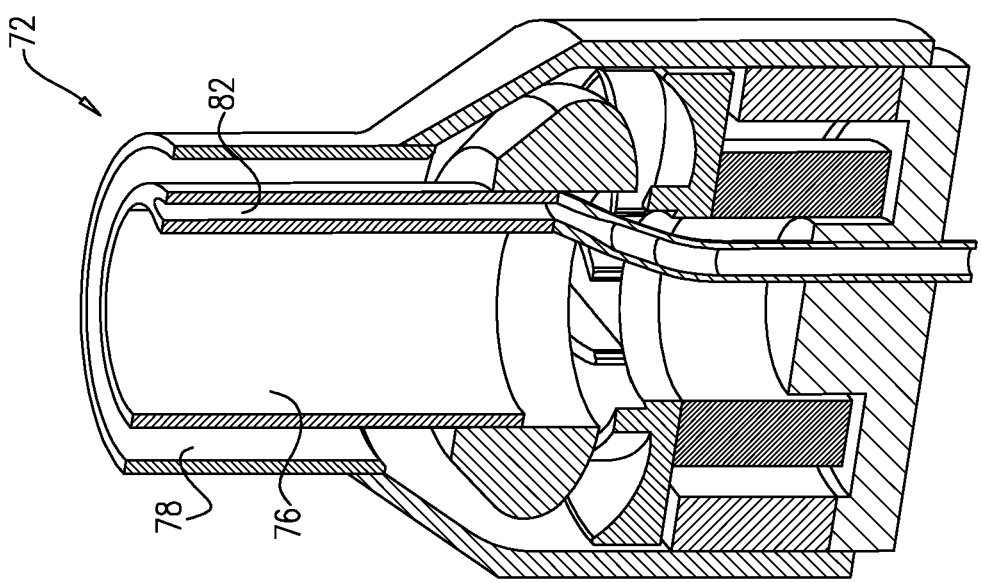

Reference is now made to FIG. 7A, which is a schematic illustration of a ventricular assist device 70 that includes a centrifugal pump 72, in accordance with some applications of the present invention. Reference is also made to FIGS. 7B and 7C, which show, respectively, three-dimensional and two-dimensional cross-sectional views of the centrifugal pump, in accordance with some applications of the present invention.

For some applications, ventricular assist device assists pumping of a ventricle (e.g., left ventricle 22) by using centrifugal pump to pump blood from the subject's left ventricle, out of the subject body, and into the subject's aorta 30. For some applications, a catheter 74 is inserted into the subject's vasculature that extends from centrifugal pump 72 to the subject's ventricle. As shown in FIGS. 7B and 7C, typically, catheter 74 defines concentric tubes 76 and 78. Blood is pumped out of the subject's left ventricle via a first one of concentric tubes (e.g., inner tube 76, as indicated by the dashed arrows indicating the direction of blood flow in FIG. 7C), and blood is pumped into the subject's aorta via a second one of the concentric tubes (e.g., outer tube 78, as shown in FIG. 7C). Typically, the first and second tubes are inserted into the subject's body via a single insertion point, e.g., femoral artery 80, as shown in FIG. 7A, or via a different insertion point, such as the subclavian artery. For some applications, centrifugal pump 72 defines an additional tube 82, via which blood pressure is measured.

The scope of the present invention includes combining any of the apparatus and methods described herein with any of the apparatus and methods described in one or more of the following applications, all of which are incorporated herein by reference:

International Patent Application PCT/IL2017/051092 to Tuval (published as WO 18/061002), filed Sep. 28, 2017, entitled "Blood vessel tube," which U.S. Provisional Patent Application 62/401,403 to Tuval, filed Sep. 29, 2016;

International Patent Application PCT/IL2016/050525 to Schwammenthal (published as WO 16/185473), filed May 18, 2016, entitled "Blood pump," which claims priority from US Provisional Patent Application 62/162,881 to Schwammenthal, filed May 18, 2015, entitled "Blood pump;"

International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. patent application Ser. No. 14/567,439 to Tuval (published as US 2015/0157777), filed Dec. 11, 2014, entitled "Curved catheter," which claims priority from U.S. Provisional Patent Application 61/914,470 to Tuval, filed Dec. 11, 2013, entitled "Curved catheter;" and International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

There is therefore provided, in accordance with some applications of the present invention, the following inventive concepts:

Inventive concept 1. Apparatus comprising:
a left ventricular assist device configured to assist left ventricular functioning of a subject, the left ventricular assist device comprising:
an elongate tube configured to traverse an aortic valve of the subject, such that a proximal end of the tube is disposed within an aorta of the subject and a distal end of the tube is disposed within a left ventricle of the subject, the elongate tube comprising:
a frame formed from a shape-memory alloy; and
a blood impermeable material that is disposed upon the frame;
a rotatable impeller configured to pump blood from the subject's left ventricle to the subject's aorta by rotating; and
a plurality of winged projections that are coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

Inventive concept 2. The apparatus according to inventive concept 1, wherein the elongate tube is configured to be inserted into a body of the subject transcatheterally, while in a radially-constrained configuration, and wherein the winged projections are configured to become folded, when the elongate tube is in its radially-constrained configuration.

Inventive concept 3. A method comprising:
placing an elongate tube into a body of a subject, such that the elongate tube traverses an aortic valve of the subject, such that a proximal end of the tube is disposed within an aorta of the subject and a distal end of the tube is disposed within a left ventricle of the subject, the elongate tube including:
a frame formed from a shape-memory alloy, and
a blood impermeable material that is disposed upon the frame; and
pumping blood from the subject's left ventricle to the subject's aorta by rotating an impeller that is disposed within the elongate tube,
a plurality of winged projections being coupled to the elongate tube such that planes defined by the winged projections are parallel with a longitudinal axis of the elongate tube, the winged projections being configured to stabilize turbulent blood flow that is generated by rotation of the impeller, by directing blood flow along a direction of the longitudinal axis of the elongate tube.

Inventive concept 4. The method according to claim inventive concept 3, wherein placing the elongate tube into the subject's body comprises placing the elongate tube into the subject's body transcatheterally while the elongate tube is in a radially-constrained configuration, the winged projections being configured to become folded, when the elongate tube is in its radially-constrained configuration.

Inventive concept 5. Apparatus comprising:
a left ventricular assist device configured to assist left ventricular functioning of a subject, the left ventricular assist device comprising:
an elongate tube configured to traverse an aortic valve of the subject, such that a proximal end of the tube is disposed within an aorta of the subject and a distal end of the tube is disposed within a left ventricle of the subject, the elongate tube comprising:
a frame formed from a shape-memory alloy; and
a blood impermeable material that is disposed upon the frame; and a pump comprising a rotatable impeller and a cage disposed around the rotatable impeller,
the cage being integrally formed with the elongate tube such that the cage is disposed within the frame of the elongate tube at the proximal end of the elongate tube, the pump thereby being disposed within a proximal portion of the elongate tube, and a longitudinal axis of the pump thereby being aligned with a longitudinal axis of the elongate tube.

Inventive concept 6. A method comprising:
placing, into a subject's body, a left ventricular assist device configured to assist left ventricular functioning of a subject, the left ventricular assist device including:
an elongate tube configured to traverse an aortic valve of the subject, such that a proximal end of the tube is disposed within an aorta of the subject and a distal end of the tube is disposed within a left ventricle of the subject, the elongate tube including:
a frame formed from a shape-memory alloy, and
a blood impermeable material that is disposed upon the frame, and
a pump comprising a rotatable impeller and a cage disposed around the rotatable impeller,
the cage being integrally formed with the elongate tube such that the cage is disposed within the frame of the elongate tube at the proximal end of the elongate tube, the pump thereby being disposed within a proximal portion of the elongate tube, and a longitudinal axis of the pump thereby being aligned with a longitudinal axis of the elongate tube; and
pumping blood from the subject's left ventricle to the subject's aorta by rotating the impeller, Inventive concept 7. A blood pump for pumping blood from a first location in a body of a subject to a second location in the subject's body, the blood pump comprising:
a first tube for pumping the blood away from the first location;
a second tube for pumping the blood toward to second location, the first and second tubes being coaxial with respect to each other; and
a centrifugal pump configured to pump the blood through the first and second tubes.

Inventive concept 8. A method comprising:
pumping blood from a first location in a body of a subject to a second location in the subject's body, by:
pumping the blood away from the first location via a first tube;
pumping the blood toward to second location via a second tube, the first and second tubes being coaxial with respect to each other; and
using a centrifugal pump to pump the blood through the first and second tubes.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
a tube configured to traverse an aortic valve of a subject, such that a proximal end of the tube is disposed within an aorta of the subject and a distal end of the tube is disposed within a left ventricle of the subject, the tube comprising a blood-impermeable material;
an impeller disposed inside the tube;
a frame disposed around the impeller within at least a portion of the tube;
the impeller configured to rotate such as to pump blood from the left ventricle to the aorta, the impeller being disposed inside the tube such that, when the impeller and the tube are deployed inside the subject and prior to rotation of the impeller, a radial gap between an outer edge of the impeller and an inner surface of the tube is less than 1 mm; and
a rigid stabilizing element configured to stabilize the impeller with respect to the tube, such that, during rotation of the impeller, a radial gap between the outer edge of the impeller and the inner surface of the tube is maintained.

2. The apparatus according to claim 1, wherein the impeller is configured to be placed within the subject's left ventricle.

3. The apparatus according to claim 1, wherein the impeller comprises at least one impeller blade defined by:
a helical elongate element; and
a film of material supported at least partially by the helical elongate element.

4. The apparatus according to claim 3, wherein, when the impeller is disposed in a non-radially-constrained configuration, a pitch of the helical elongate element varies along a length of the helical elongate element.

5. The apparatus according to claim 3, wherein, when the impeller is disposed in a non-radially-constrained configuration, a pitch of the helical elongate element is greater than 1 mm.

6. The apparatus according to claim 3, wherein, when the impeller is disposed in a non-radially-constrained configuration, a pitch of the helical elongate element is less than 20 mm.

7. The apparatus according to claim 3, wherein, when the impeller and the tube are deployed inside the subject and prior to rotation of the impeller, the radial gap between the outer edge of the impeller and the inner surface of the tube is less than 0.4 mm.

8. The apparatus according to claim 3, wherein the impeller further comprises a spring disposed inside of the helical elongate element, wherein the film of material is supported between the helical elongate element and the spring to thereby define the impeller blade.

9. The apparatus according to claim 8, wherein the impeller comprises a plurality of helical elongate elements, and the film of material is supported between the plurality of helical elongate elements and the spring, such that the impeller defines a plurality of blades.

10. The apparatus according to claim 8, wherein the impeller is configured to be radially constrained by the helical elongate element and the spring being axially elongated, and wherein in response to the axial elongation of the helical elongate element and the spring, the film is configured to change shape without the film of material breaking.

11. The apparatus according to claim 8, wherein the rigid stabilizing element comprises the spring, and wherein the spring, when disposed in a non-radially-constrained configuration thereof, is configured by virtue of its rigidity, to stabilize the impeller with respect to the tube, during rotation of the impeller, such that the radial gap between the outer edge of the impeller and the inner surface of the tube is maintained.

12. The apparatus according to claim 8, wherein:
the spring defines a lumen therethrough,
the impeller further comprises proximal and distal bushings; and
the rigid stabilizing element comprises a rigid shaft configured to extend from the proximal bushing to the distal bushing via the lumen defined by the spring, the rigid shaft being configured to stabilize the impeller with respect to the tube, during rotation of the impeller, such that the radial gap between the outer edge of the impeller and the inner surface of the tube is maintained.

13. The apparatus according to claim 8, wherein the spring, when disposed in a non-radially-constrained configuration thereof, is configured such that there are substantially no gaps between windings of the spring and adjacent windings thereto.

14. The apparatus according to claim 1, further comprising a plurality of winged projections that are coupled to the frame and that are configured to rectify blood flow that is generated by rotation of the impeller, by directing blood flow toward a direction of the longitudinal axis of the tube.

15. The apparatus according to claim 14, wherein the tube is configured to be inserted into a body of the subject transcatheterally, while in a radially-constrained configuration, and wherein the winged projections are configured to become folded, when the tube is in its radially-constrained configuration.

16. A method, comprising:
placing a tube into a body of the subject, such that the tube traverses an aortic valve of the subject, such that a proximal end of the tube is disposed within an aorta of the subject and a distal end of the tube is disposed within a left ventricle of the subject, the tube including a blood impermeable material,
an impeller disposed inside the tube,
a frame being disposed around the impeller within at least a portion of the tube, and
the impeller being disposed inside the tube, such that when the impeller and the tube are deployed inside the subject's body and prior to rotation of the impeller, there is a radial gap of less than 1 mm between an outer edge of the impeller and an inner surface of the tube, and
a rigid stabilizing element being configured to stabilize the impeller with respect to the tube;
rotating the impeller, such as to pump blood from the subject's left ventricle to the subject's aorta,
wherein the rigid stabilizing element maintains a radial gap between the outer edge of the impeller and the inner surface of the tube, during the rotation of the impeller.

17. The method according to claim 16, wherein the impeller is disposed inside the tube, such that when the impeller and the tube are deployed inside the subject's body and prior to rotation of the impeller, there is a radial gap of less than 0.4 mm between the outer edge of the impeller and the inner surface of the tube.

18. The method according to claim 16, wherein the impeller includes at least one impeller blade defined by:
a helical elongate element; and
a film of material supported at least partially by the helical elongate element.

19. The method according to claim 18, wherein the impeller includes a spring disposed inside the helical elongate element, and the film of material is supported between the helical elongate element and the spring, such as to define a blade of the impeller.

20. The method according to claim 19, wherein the rigid stabilizing element includes the spring and rigidity of the spring is used to stabilize the impeller with respect to the tube, during rotation of the impeller.

21. The method according to claim 19, wherein the impeller includes proximal and distal bushings and the rigid stabilizing element includes a rigid shaft that extends from the proximal bushing to the distal bushing via a lumen defined by the spring.

* * * * *